United States Patent [19]

Palm et al.

[11] Patent Number: 5,869,970

[45] Date of Patent: Feb. 9, 1999

[54] POWER MANAGEMENT SYSTEM FOR AN IMPLANTABLE DEVICE

[75] Inventors: William A. Palm, Minnetonka; Lloyd A. Van Hofwegen, New Brighton; Jean-Cheui Hsung, Shoreview; Michael W. Dooley, Minneapolis; Keith R. Maile, Lino Lakes; William J. Linder, Golden Valley; David W. Kelly, Lino Lakes; Jeffrey Laackmann, Isanti; Richard J. Wessels, Vadnais Heights, all of Minn.

[73] Assignee: Cardiac Pacemakers, Inc., St. Paul, Minn.

[21] Appl. No.: 550,835

[22] Filed: Oct. 31, 1995

[51] Int. Cl.⁶ .............................. A61N 1/37; A61N 1/378
[52] U.S. Cl. .............................. 324/433; 607/28; 607/29
[58] Field of Search ..................... 324/426, 429, 324/432, 433, 436; 607/16, 27, 28, 29

[56] References Cited

U.S. PATENT DOCUMENTS

| | | | |
|---|---|---|---|
| 4,031,899 | 6/1977 | Renirie | 128/419 |
| 4,323,075 | 4/1982 | Langer | 128/419 |
| 4,345,604 | 8/1982 | Renirie | 128/419 |
| 4,548,209 | 10/1985 | Wielders et al. | 128/419 |
| 4,830,006 | 5/1989 | Haluska et al. | 128/419 |
| 4,868,908 | 9/1989 | Pless et al. | 323/267 |
| 4,952,864 | 8/1990 | Pless et al. | 323/299 |
| 5,083,562 | 1/1992 | de Coriolis et al. | 128/419 |
| 5,265,588 | 11/1993 | Nelson | 607/5 |
| 5,285,779 | 2/1994 | Cameron et al. | 607/5 |
| 5,488,553 | 1/1996 | Renger | 363/21 |

OTHER PUBLICATIONS

E.S. Takeuchi, "Lithium/Silver Vanadium Oxide Batteries for Implantable defibrillators," *PACE*, 11, pp. 2035–2039, (Nov. 1988).

E.S. Takeuchi et al., "Energy Storage and Delivery," *Implantable Cardioverter–Defibrillators: A Comprehensive Textbook*, edited by N.A. Mark Estes III et al., pp. 123–132, (1994).

*Primary Examiner*—Michael Brock
*Attorney, Agent, or Firm*—Schwegman, Lundberg, Woessner & Kluth, P.A.

[57] ABSTRACT

A power management system for an implantable device is disclosed. One application is an implantable cardioverter/ defibrillator. Charging circuits for implantable cardioverter/ defibrillators require relatively large currents from the power supply. The present power management system provides extended device operation and reduced charge cycle time. The present system monitors both current and voltage drawn from the power supply to prevent a loss of system voltage. Elective replacement indication is performed using charging information provided by the present power management system.

17 Claims, 24 Drawing Sheets

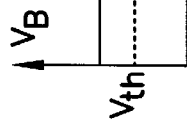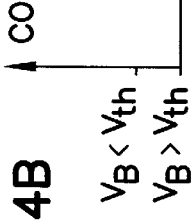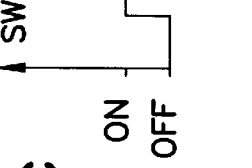

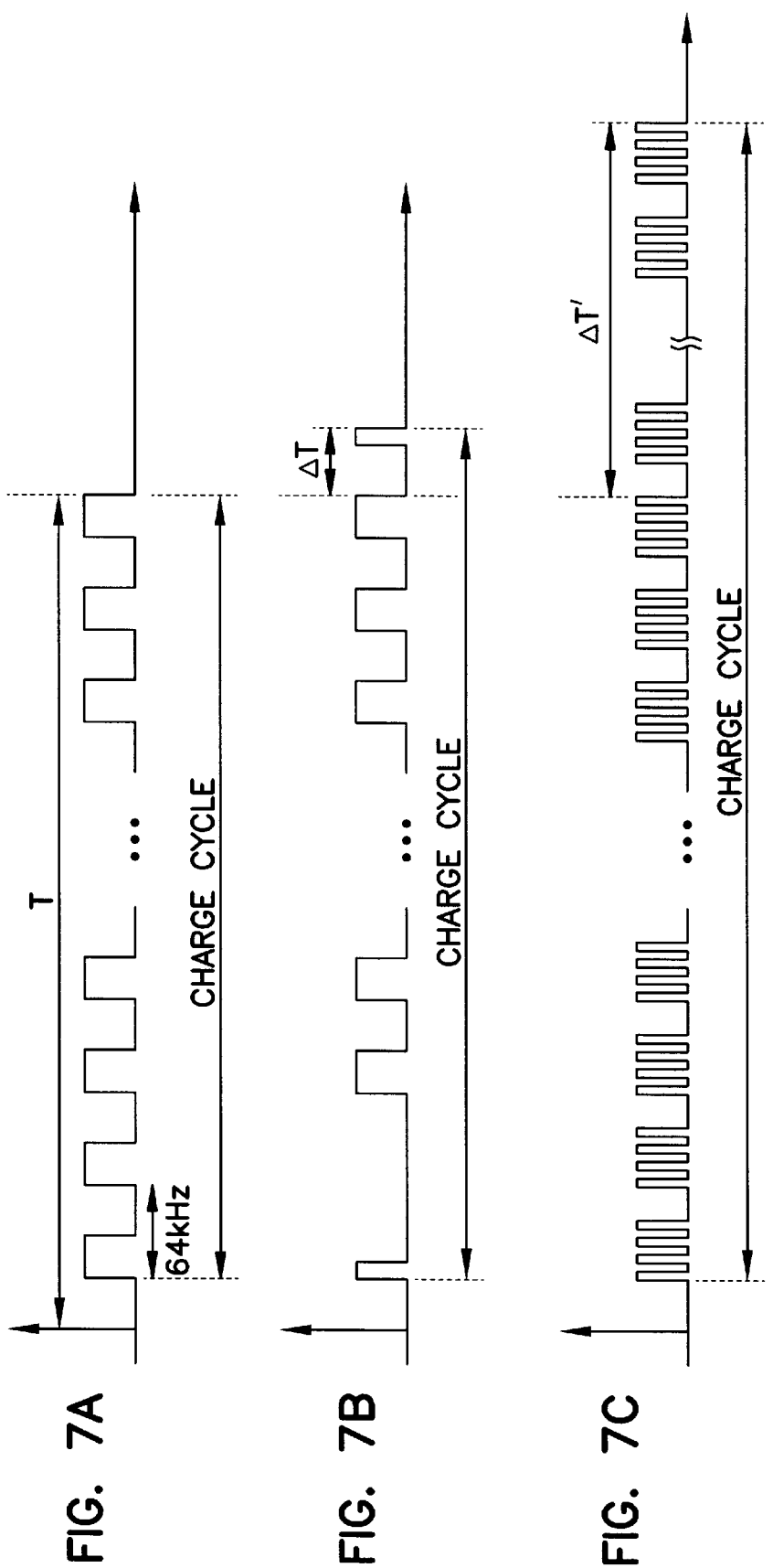

POWER MANAGEMENT SYSTEM FOR AN IMPLANTABLE DEVICE

FIELD OF THE INVENTION

The present invention relates generally to power management systems for battery-powered devices and in particular to a power management system for an implantable devices.

BACKGROUND

Implantable devices require compact power sources and energy efficient electronics for prolonged device operation. Battery-powered devices must be explanted each time the power supply fails or reaches end of life ("EOL"). Ideally, the power management system of a battery-powered implantable device optimizes battery utilization by controlling battery consumption and by providing an elective replacement indicator ("ERI") which provides sufficient notice to the patient's doctor that end of life is near without prematurely declaring ERI.

Several methods have been suggested for an ERI, however, battery characteristics vary and an accurate ERI is needed in the art. Generally speaking, internal battery resistance increases as the battery is used, however, transient internal resistances have been observed which vary in a complex function of battery life and history of current draw. The internal battery resistance will be called the "steady state internal resistance" throughout this document to distinguish it from the transient internal resistance. As stated before, the steady state internal resistance does vary with current consumption, and is therefore a function of current drawn from the cell, but it changes due to mechanisms which differ from the transient internal resistance mechanisms.

Furthermore, none of the previous power management systems have addressed a specific problem found in lithium-silver-vanadium-pentoxide batteries which arises when current is extracted from the battery in certain portions of the battery life curve. A lithium-silver-vanadium-pentoxide battery exhibits an abrupt increase in internal resistance in certain periods of battery life due to formation of a "passivation layer" on the lithium surface following periods of relatively low current draw from the battery. The passivation layer creates a transient resistance which diminishes when current is drawn from the battery.

This effect is called "voltage delay" since the output voltage of the battery drops significantly upon current demand due to a large transient internal battery resistance. As current is extracted from the battery, the transient internal resistance is diminished and the output voltage of the battery returns to the ordinary output voltage for that portion of the battery lifetime.

The voltage delay effect may lower the battery output voltage below the reset voltage of the device electronics during high initial current draw. Even if the output voltage of the power source does not initially drop below the reset voltage the pulse delivery circuit may never draw enough energy to completely charge the high voltage output circuit due to a large steady state internal resistance of the battery.

Another problem with the previous power systems in implantable devices is that as the battery (or batteries, for multiple battery devices) approaches its EOL, the battery has increasing difficulty in providing adequate charge to the output capacitor to deliver a therapy pulse. Therefore, explantation and replacement of the device is performed earlier than necessary. The battery erroneously appears to have reached EOL because as current is drawn the voltage delay provides sufficient transient internal resistance to reduce the terminal voltage of the battery so as to signal elective replacement of the battery.

Therefore, there is a need in the art for an implantable power management system which extracts current from the power supply without requiring premature device replacement and without risking a reset of device hardware. The power system should also manage steady state internal battery resistance to ensure that the power supply can deliver a complete therapy pulse or, alternatively, signal the patient that the power supply is unsafe for charging the output circuits. There is yet further a need in the art for a power system which manages the transient internal battery resistance synonymous with the voltage delay effect so as to maximize battery life and reduce the number of device replacements.

SUMMARY OF THE INVENTION

The present invention includes several embodiments which provide a method and apparatus for a power management system for an implantable device, however, the teachings of the present disclosure apply equally to any device having a power supply with a variable internal resistance. For purposes of illustration, the present invention is described in the application of a power management system for an implantable cardioverter/defibrillator (ICD), however, the present invention is applicable to any battery powered device.

Most high voltage pulse delivery devices incorporate a power inverter to multiply the output voltage of the power supply. In devices having a flyback transformer energy is transferred to the output stage by periodically switching the output voltage of the power supply across the primary winding of the flyback transformer. The charging function requires substantially larger currents from the power supply than required by monitoring functions and the resulting voltage drop across the internal resistance of the power supply may result in the power supply output voltage falling below the reset voltage of the device circuits. Operation of the control circuits becomes unpredictable and unreliable when the supply output voltage approaches their reset voltage.

When the power supply is a battery, the internal battery resistance is a complex function of the battery physics and includes steady state internal resistance and a transient internal resistance. The steady state resistance is the increasing internal resistance of a battery over usage of the battery, absent the voltage delay effect. The transient resistance is the resistance caused by the passivation layer and is the source of the voltage delay effect.

In one embodiment, the power management system in an ICD uses a comparator to signal when the supply voltage drops below a predetermined threshold. The ICD control electronics pause charging until the power supply voltage exceeds a predetermined threshold. In this embodiment, electronics are used to record the time intervals when the charging activity was halted. In one embodiment, the amount of pause time per each charge cycle is accumulated. In another embodiment, the total charge time for each charge cycle is accumulated. The accumulated data may be used in an ERI system and for accurate determination of ERT.

In another embodiment the power management system incorporates a latch to determine whether the power supply voltage fell below the threshold while the microprocessor was performing other duties.

In yet another embodiment, a specialized control circuit is employed to sense when the supply voltage fell below the predetermined threshold. The specialized control circuit is designed for rapid recognition of the transition of the output voltage below the threshold. This allows for pulse-by-pulse control of the charging activity.

BRIEF DESCRIPTION OF THE DRAWINGS

In the drawings, where like numerals describe like components throughout the several views:

FIG. 4A, FIG. 4B, and FIG. 4C are plots of the switching signal and comparator output as a function of the battery voltage and threshold voltage according to one embodiment of the present invention;

FIG. 7A is a plot of the switching signal for a battery at beginning of life;

FIG. 7B is a plot of the switching signal for a system demonstrating front end nibbling;

FIG. 7C is a plot of the switching signal for a system demonstrating back end nibbling;

DETAILED DESCRIPTION

In the following Detailed Description, reference is made to the accompanying drawings which form a part hereof and in which is shown by way of illustration specific embodiments in which the invention may be practiced. These embodiments are described in sufficient detail to enable those skilled in the art to practice and use the invention, and it is to be understood that other embodiments may be utilized and that electrical, logical, and structural changes may be made without departing from the spirit and scope of the present invention. The following detailed description is, therefore, not to be taken in a limiting sense and the scope of the present invention is defined by the appended claims.

For the following description, the following definitions apply:

EOL or "end of life" is the condition where the battery powered device will no longer operate reliably due to degradation of the battery or batteries powering the device.

ERI or "elective replacement indicator" is a system for signalling that elective replacement should be performed and that the system is approaching EOL.

ERT or "elective replacement time" is the point of operation whereby elective replacement is suggested and signalled by the ERI. ERT precedes EOL, but the amount of margin depends on the ERI used and the metrics by which the ERI declares ERT.

"Battery" refers to any single cell or collection of cells. The embodiments herein describe both single battery and multiple battery embodiments.

Figure 1:
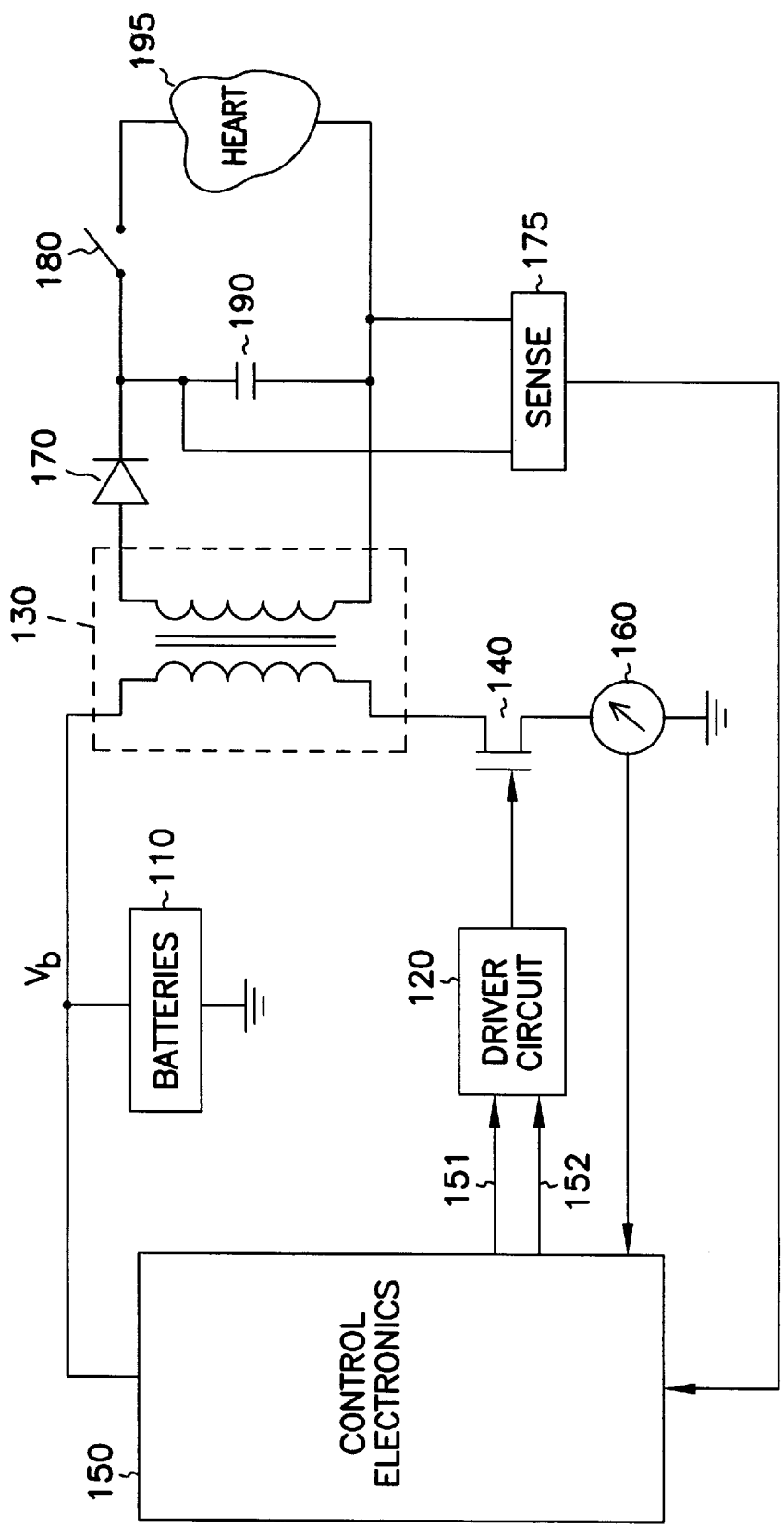
FIG. 1 is a schematic diagram of a pulse delivery device which is one environment in which the present invention may be practiced.

One example of a pulse delivery device is shown in FIG. 1, which is one environment in which the present invention may be practiced. In this example, batteries 110 are switched in series with the primary winding of inverter/transformer 130 to produce a current in the primary winding and build up flux in the core of the inverter/transformer 130 for delivery to capacitor 190. Inverter/transformer 130 serves as a "flyback" transformer which charges by switching the current through the primary by toggling switch 140 via driver circuit 120. Diode 170 ensures that flux is stored in the core of inverter/transformer 130 while switch 140 is conducting. When switch 140 becomes nonconducting the flux stored in the core is converted into current which passes through diode 170 to charge capacitor 190. This process of building up flux while switch 140 conducts, and then charging capacitor 190 after the switch is opened is repeated several times to build up enough charge on capacitor 190 for a therapy pulse.

A sense circuit 175 detects when capacitor 190 is fully charged and transmits a signal to control electronics 150.

Control electronics 150 then closes the switch 180 to deliver a therapy pulse to the patient's heart 195 (or other body tissue).

In one embodiment, the driver circuit 120 generates a 64 KHz pulse train when enabled by the control electronics 150 via enable line 152. In this embodiment the switch signal from driver circuit 120 is a periodic pulsetrain which is enabled by enable line 152. In yet another embodiment, pulse strobe line 151 may be used to generate asynchronous pulses from driver circuit. One such embodiment is offered for demonstration in FIG. 5, where pulses may originate synchronously from the 64 KHz clock 510 or asynchronously from assertion of pulse generation electronics 512 via pulse strobe line 151 by control electronics 150.

In another embodiment, the pulses applied to switch 140 are functions of the current sourcing capability of batteries 110, which varies as the batteries 110 age. One example of such a scheme employs current monitor 160 and control electronics 150 to limit current amplitude of the primary current by switching switch 140 off when the primary current reaches a predetermined maximum value. This method generates shorter switching pulses when the batteries 110 are new and longer pulses as the batteries 110 age; it takes longer for the batteries 110 to source the maximum current due to the increasing internal resistance of the batteries 110.

Alternate embodiments combine the current monitoring aspect with a fixed time base to determine how long a pulse should be applied to switch 140 and how long the control electronics will wait until asserting another pulse. For example, in one embodiment the time base is used to synchronize assertion of a switching pulse and the current limitation method is used to terminate the pulse. Assertion of a following pulse occurs synchronously with the time base, and the pattern is repeated.

In yet another embodiment, the pulses applied to switch 140 are generated by a self oscillating pulse generation scheme, which is discussed in further detail in the section entitled "An Alternate Embodiment of a Power Management System", below.

The example in FIG. 1 demonstrates a power source having multiple batteries 110, however, a single battery or cell may be used, as long as the battery or cell is able to produce sufficient charge current through the primary winding of inverter/transformer 130 and provide sufficient voltage to control electronics 150.

Battery Characteristics and Voltage Delay

In one embodiment batteries 110 are a pair of series connected WGL 8513 Lithium-Silver-Vanadium-Pentoxide batteries. The WGL 8513 Lithium-Silver-Vanadium-Pentoxide battery is available from Wilson Greatbatch, Inc. Those skilled in the art will readily recognize that other batteries may be substituted without departing from the scope and spirit of the present invention. In addition, there is no need to refer to a plurality of batteries to demonstrate the present invention, and another embodiment will be described below which incorporates a single battery.

Figure 2:
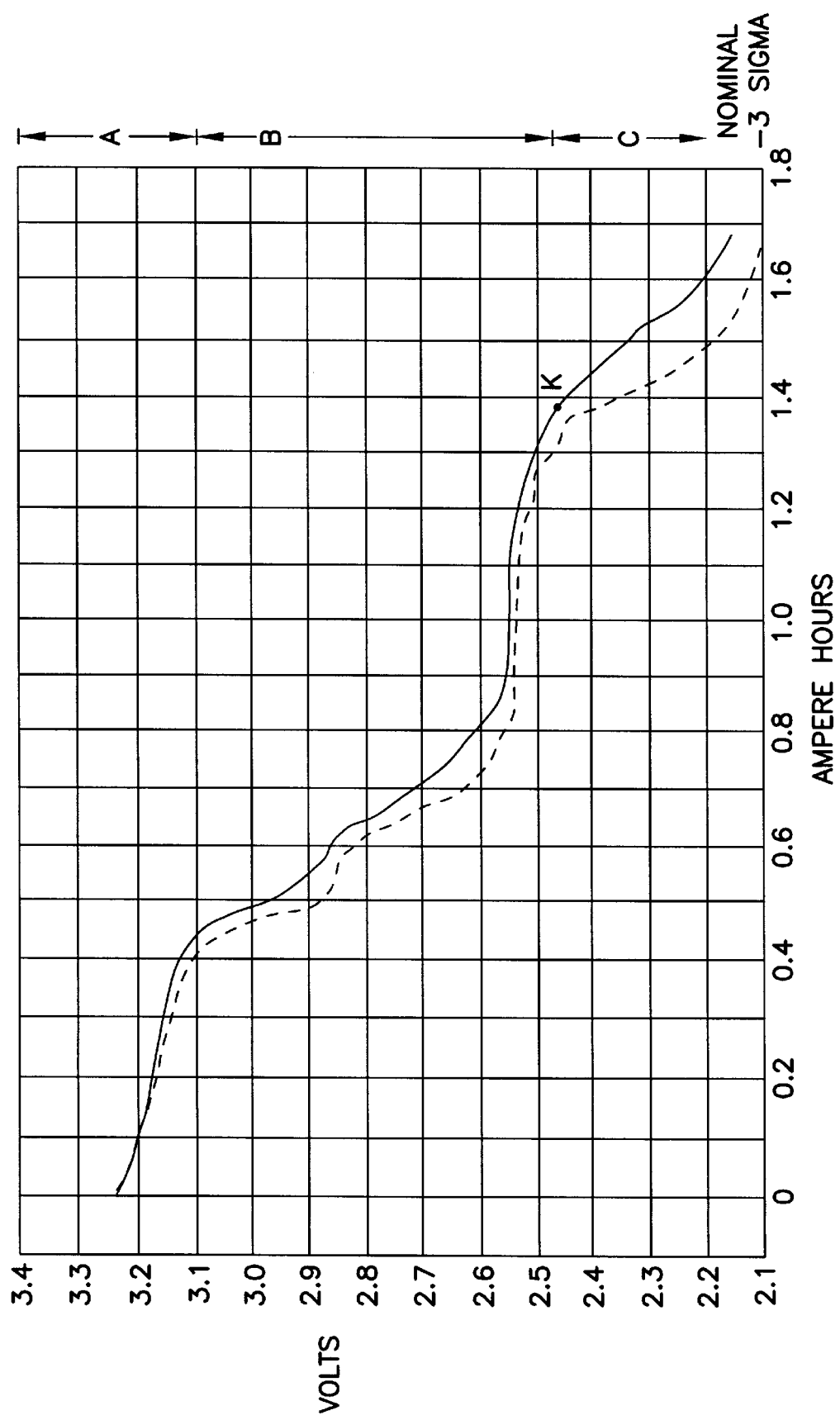
FIG. 2 is a plot of battery open circuit voltage versus current multiplied by time.

FIG. 2 shows an open circuit voltage plot as a function of current output multiplied by time (ampere hours) for the WGL 8513 battery. Those skilled in the art will readily recognize that the present battery curve is used to demonstrate one application of one embodiment of the present power management system and that the system demonstrated herein may be practiced using other batteries having different battery curves without departing from the scope and spirit of the present invention. The example provided herein is intended to demonstrate one embodiment of the present system, and is not intended a limiting or exclusive sense.

The battery curve of FIG. 2 has been divided into three regions to simplify explanation of the operation of the present system. The divisions herein are approximate and other divisions may be made without departing from the present system. Region A is approximately the battery's "beginning of life" or BOL, and it extends from 3.4 volts to approximately 3.1 volts for this particular battery. Region B is approximately "middle of life" or MOL. Voltages of approximately 3.1 to 2.75 volts are labeled MOL1 and voltages between 2.75 volts and 2.45 volts are labeled MOL2. Region C is approximately where elective replacement is declared and ranges from 2.45 volts to 2.2 volts. Two voltages have been identified in region C to assist in declaring the end of the battery's useful life. The first voltage, ERT1, is approximately 2.45 volts and the second voltage, ERT2, is approximately 2.2 volts. The battery exhibits relatively large internal impedance and large rate of increasing resistance at output voltages under 2.2 volts. The rapid falloff of the battery curve at voltages under 2.2 volts limits the usage of the battery in this voltage range.

To maximize battery performance the power management system must exploit regions B and C to extend effective battery life. Use of the battery through these regions is complicated by the transient internal resistance which is prominent in these regions and is the cause of the voltage delay effect. This "transient" internal resistance is current dependent and is reduced after a heavy current demand is imposed on the batteries. For example, the typical internal resistance of a pair of series connected WGL 8513 batteries is approximately 0.5 ohms. At approximately 1300 mA-hrs the combined series internal resistance is approximately 1.0 ohm. The increase in internal resistance is not linear with time, and at approximately 800 mA-hrs resistances of approximately 2.0 ohms are observed which are transient. These transient resistances disappear in less than a second if an amp is drawn from the batteries.

Hence, the term "voltage delay" is used, since the output voltage of the battery is reduced due to a voltage drop across the transient portion of the internal resistance of the battery. The output voltage increases as current is drawn from the battery, since the transient portion of the resistance disappears as current is drawn from the battery. The output voltage reaches its steady state output voltage after the transient portion of the resistance vanishes. Of course, this "steady state" output voltage is a function of the internal battery impedance as a function of battery life. The exact mechanisms responsible for the transient resistance are not known.

In devices where an elective replacement indicator (ERI) is determined by tracking output voltage of the battery, failure to account for the voltage delay effect results in premature declaration of EOL (i.e., the battery is deemed to be at EOL before the usable portion of the battery life is exploited). This means unnecessary replacement of the device and greater risk to the patients who undergo surgery for the early replacement.

If the transient resistance is not properly managed the magnitude of the transient resistance multiplied by a high current demand may be sufficient to decrease the battery output voltage to a voltage which is below the reset voltage of the control electronics. Therefore, without management of the transient resistance, the entire device may fail as a result of a high current demand in the portions of battery life where voltage delay is experienced.

The present power management system manages the transient portion of internal battery resistance to fully exploit the current sourcing capabilities of the battery. The output battery voltage is monitored while current is drawn from the battery to control the output voltage and prevent a reset event from occurring. The voltage delay effect is ameliorated, since the battery's transient internal resistance is decreased as current is drawn. Capacitor recharge times are increased by the management of current draw in region C, however, effective battery lifetime is longer.

One Embodiment of a Power Management System

Figure 3:
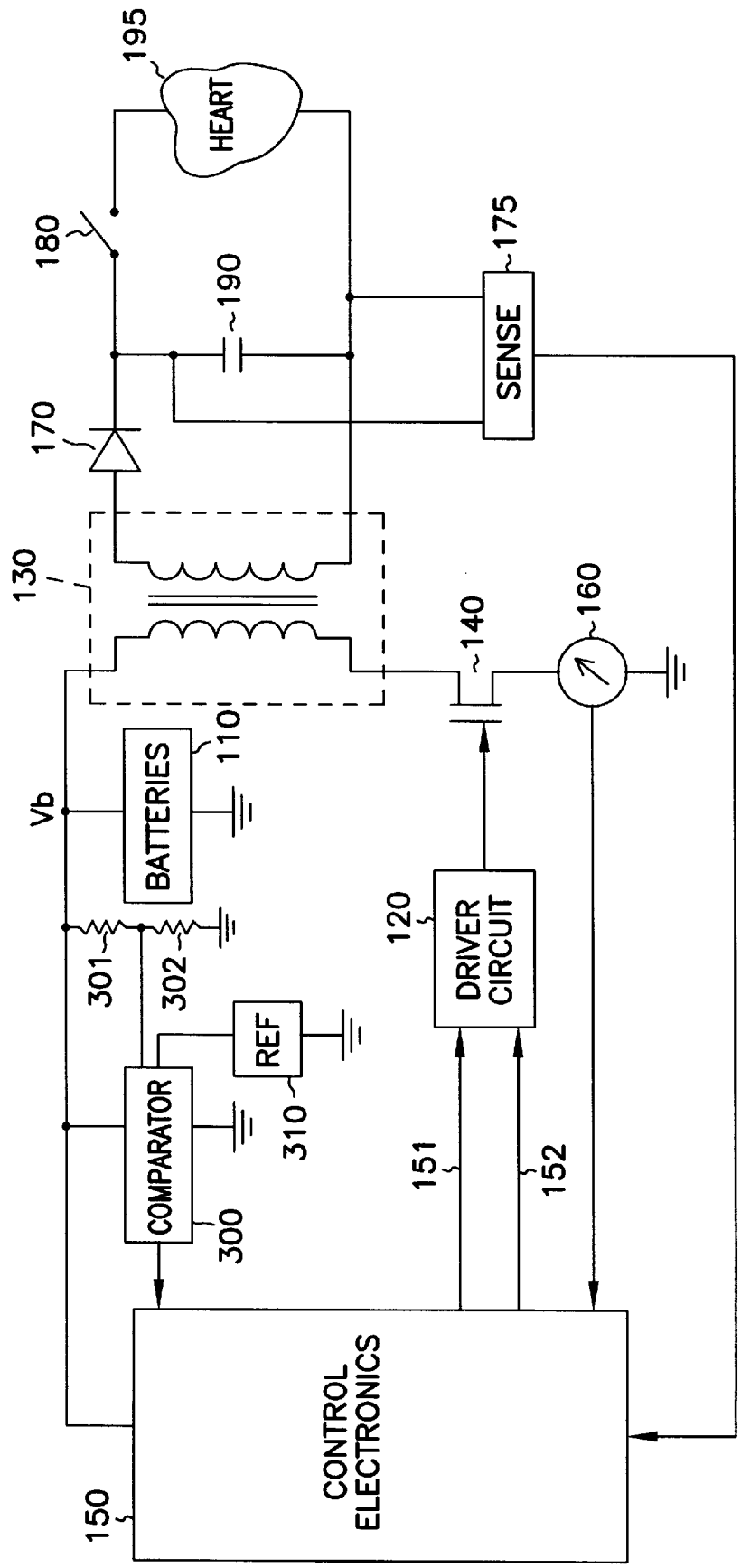
FIG. 3 is a block diagram of a battery management system for a pulse delivery device according to one embodiment of the present invention.

One application of the present system is shown in FIG. 3. New batteries 110 have an output voltage which exceeds the threshold voltage while charging the invertor/transformer 130, so the system will charge output capacitor 190 by any of the above-described pulse generation methods. In one embodiment, the pulses are generated to provide adequate time for the charging current through the primary of transformer 130 to reach a peak current, Ip. Ip is preselected to provide an average primary winding current which is the charging current recommended by the manufacturer of the batteries 110. In one embodiment Ip is set to about 4 Amps to provide an average primary current of 2 Amps, since the primary current waveform is approximately a ramp from zero Amps at the beginning of the switch pulse to 4 Amps at the end of the pulse.

Comparator 300 compares the output voltage, Vb, of the batteries 110 to a reference voltage 310. The reference voltage is set to a threshold value which is above the reset voltage of the control electronics. In one embodiment resistors 301 and 302 are used to voltage divide the voltage Vb so that the voltage reference may be a fraction of Vb, thereby providing more reliable voltage comparison. When the voltage produced by the batteries 110 falls below the threshold voltage, control electronics 150 receives a signal from comparator 300 and deactivates driver circuit 120 to open switch 140. For simplicity, the voltage of the batteries 110 will be referred to as "open circuit voltage" when the switch 140 is open, since the current draw is substantially lower for supplying the control electronics 150 with current than the current drawn when charging the inverter/transformer 130.

The batteries' output voltage Vb approaches their open circuit voltage as the switch 140 is opened. If the switch 140 is opened soon after the output voltage equals the threshold voltage the voltage Vb will remain above the reset voltage of the electronics. When the open circuit voltage exceeds the threshold voltage the comparator 300 signals the control electronics 150 to enable the switch 140 to continue charging. This procedure is repeated several times to completely charge capacitor 190 and is named "nibbling". Nibbling reduces the voltage delay effect and increases the effective lifetime of the batteries 110 since it allows the system to extract current from the batteries without the output voltage dropping dangerously close to the reset voltage of the electronics. However, nibbling may extend the time needed to charge the capacitor 190.

A suitable threshold voltage provides adequate voltage margin over the reset voltage of control electronics and is also within the range of closed circuit voltages (i.e., the output voltages of the batteries during charging) expected when the batteries are capable of experiencing voltage delay. FIG. 2 shows the open circuit voltage for a single battery. The closed circuit voltage of a battery is less than the open circuit voltage due to the voltage dropped over the internal resistance of the battery. In one embodiment, where the batteries 110 comprise two series-connected WGL 8513 batteries, an example of a suitable threshold voltage is 3.2 volts. Several different threshold voltages are possible, and this example is provided to demonstrate the operation of one embodiment of the present system.

The interaction of the battery voltage, Vb, comparator 300, and switch 140 are shown in FIGS. 4A, 4B, and 4C, respectively, for one embodiment of the present invention. In certain embodiments a latency, L, in controlling the switch 140 based on the battery voltage, Vb, is imposed due to delay of the comparator circuit and of the control electronics 150 monitoring the comparator 300 output. In FIG. 4C, the latency L is shown to demonstrate that the comparator 300 may switch prior to disabling the switch 140 due to this latency, L. The latency may be a function of several variables, including, but not limited to, bandwidth of the comparator and the comparator monitoring loop, deadband of the comparator, and latency of the control electronics monitoring the comparator. The latency is also shown as L', L", and L'" to illustrate that it may vary as a function of several system variables.

The following discussion is limited to the operation of the system when the capacitor 190 is being charged. For the sake of illustration, a fixed switching pulse method will be assumed, however, the present system may be practiced by using any of the above-mentioned pulse switching methods or their equivalents. As can be seen from FIG. 4C, the switch 140 is normally switched at high frequency to charge capacitor 190 using inverter/transformer 130. The switching pulses are unmodified as long as the series battery voltages, Vb, exceed the threshold voltage, Vth, as shown in region (1). When Vb is less than Vth (trace 4A, region (2)) the comparator 300 signals to control electronics to interrupt the switching waveform, as shown in trace 4B, region (2). The switching waveform, 4C region (2), is not immediately suppressed, since latency L delays response of switch 140. When the switch 140 opens the battery voltage Vb increases due to lessening internal voltage drop from the reduced battery current, as reflected by the upward voltage excursion of Vb in trace 4A, region (2). As Vb crosses and exceeds the Vth boundary the comparator 140 returns to its original state (trace 4B, region (2)) and the switching signal is again uninhibited after a latency L' (trace 4C, region (3)). In some embodiments, if Vb crosses the Vth boundary before the 64 KHz pulse is completed, the switch will not be activated until the next 64 KHz pulse, i.e., assertion of a pulse must occur at the beginning of a synchronous interval, or the pulse is inhibited until the beginning of the next synchronous interval. Other embodiments do not synchronize assertion of the first pulse in this manner.

The waveforms in FIGS. 4A, 4B, and 4C, region (5), demonstrate operation of the system later in battery life, as the voltage delay effect is more prominent. In region (4) the battery voltage, Vb, is approximately the combined open circuit voltage of the series-connected batteries since no charging has taken place for a relatively long time. The first charging pulse is requested by the control electronics 150 in region (5), trace 4C. The voltage delay is experienced almost immediately, since the large internal resistance of the battery combined with the large transient resistance (due to the voltage delay effect) drops the output voltage of the batteries Vb as the large current is demanded from the batteries. The switching pulses are repeatedly interrupted (i.e., the pulse stream is "nibbled") by an oscillation of output voltage about the Vth boundary. If this process was monitored for a longer time the interruptions would be fewer and gradually disappear as the batteries "healed" or reduced their internal transient resistance. As described above, transient battery resistance is reduced by high current draw on batteries exhibiting the voltage delay effect.

Therefore, the nibbling process results in prolonged battery utilization without risking reset of the control electronics due to the careful battery voltage monitoring and correction provided by the present system.

In one circuit realization of the circuit in FIG. 3 the control loop, comprising the control electronics 150, driver circuit 120, switch 140, and comparator 30, imposes time delays which exceed the period of the switching signal. These delays result in the inhibition of several charging cycles per nibble event and an increase in the overall time to charge the device. However, the time delay may provide other benefits, such as collection of a number of statistics about the charging process which may be processed to provide an ERI and determine ERT, as described in an alternate embodiment below.

Figure 4D:
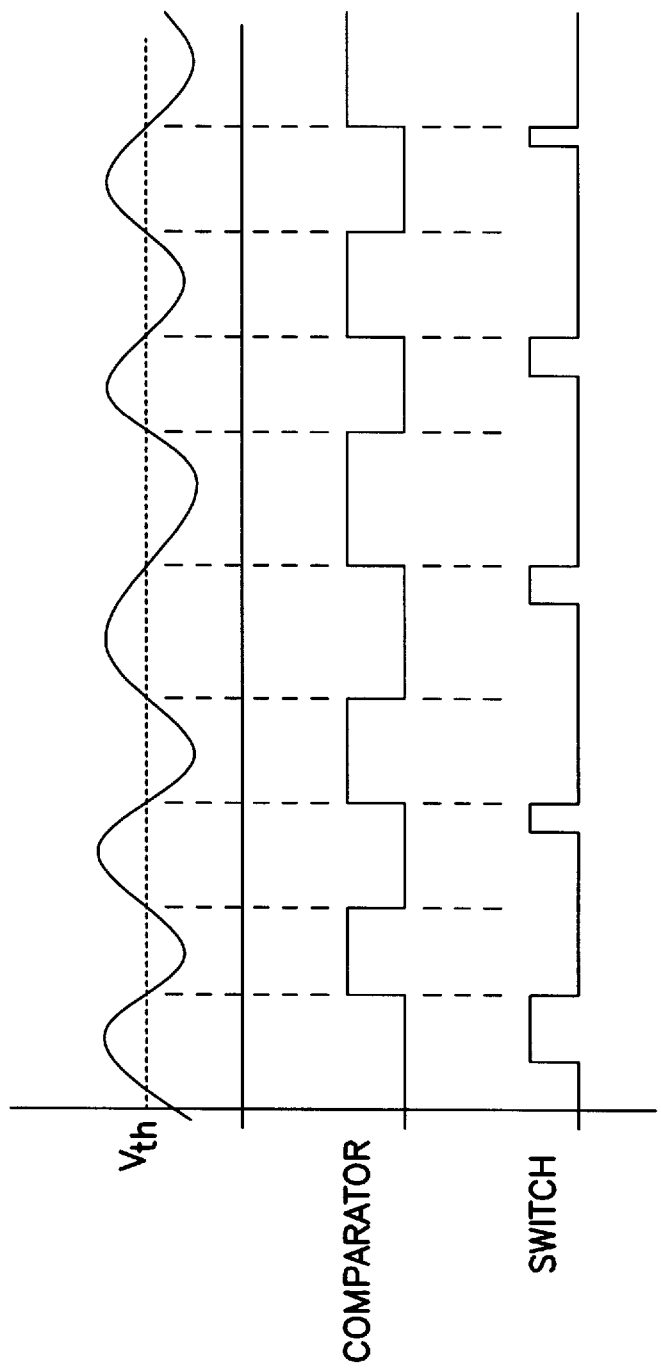
FIG. 4D is a plot of the switching signal and comparator output as a function of battery voltage and threshold voltage for an idealized system.

FIG. 4D shows a plot of the battery voltage, comparator output signal, and switching signal to demonstrate the operation of the nibbling function in an ideal system with zero closed loop delay time. A very high speed comparator circuit would provide significantly less latency than a software based system.

Figure 5A:
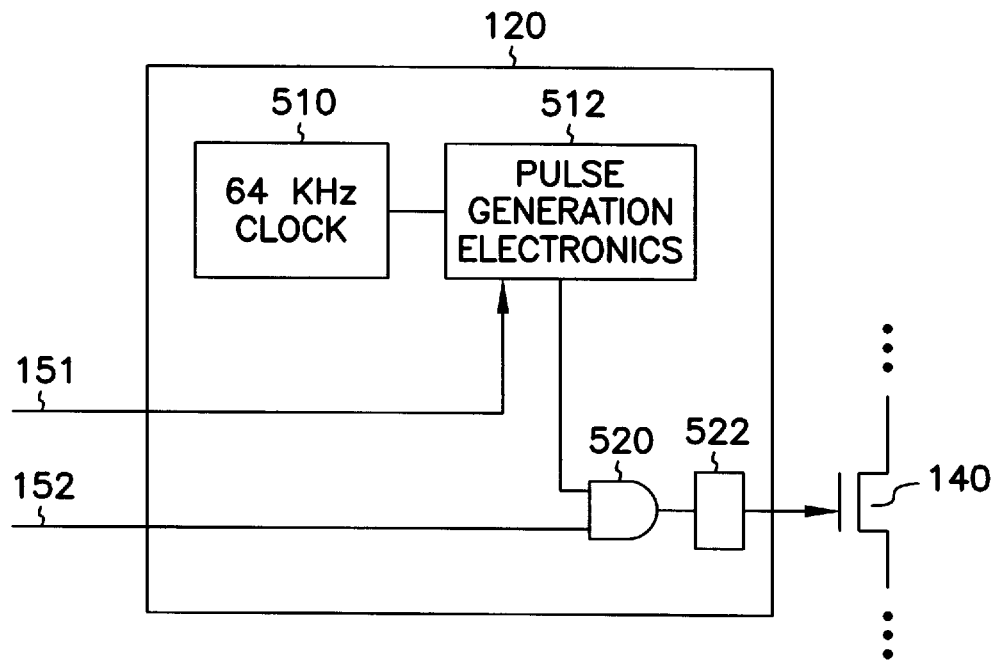
FIG. 5A is a block diagram of one embodiment of a driver circuit according to one embodiment of the present invention.

FIG. 5 shows one embodiment of a driver circuit 120 to provide the described "nibbling" of the switching signal. The 64 KHz clock 510 is constantly active, however, outputs to the switch 140 are inhibited unless the signal 152 from control electronics 150 is logic one, thereby enabling AND gate 520. The signal 152 from control electronics 150 is activated during a charging cycle and inhibited when the control electronics 150 senses a transition of the comparator 300 during a "nibbling" event. This, in turn, disconnects the batteries 110 from the inverter/transformer 130 via switch 140. Voltage step-up 522 provides adequate switching voltage for switch 140. Those skilled in the art will recognize that other embodiments of the driver circuit 120 are possible without departing from the spirit and scope of the present invention. For example, in one embodiment signal line 151 provides a means for asynchronous control of the pulse generation means. It provides a means for generating an asynchronous pulse, or for asynchronously interrupting the 64 KHz pulse stream. Other embodiments may use different configurations, input signals, and different frequency clock to provide a special switching signal.

Microprocessor-Based Battery Management System

Figure 6:
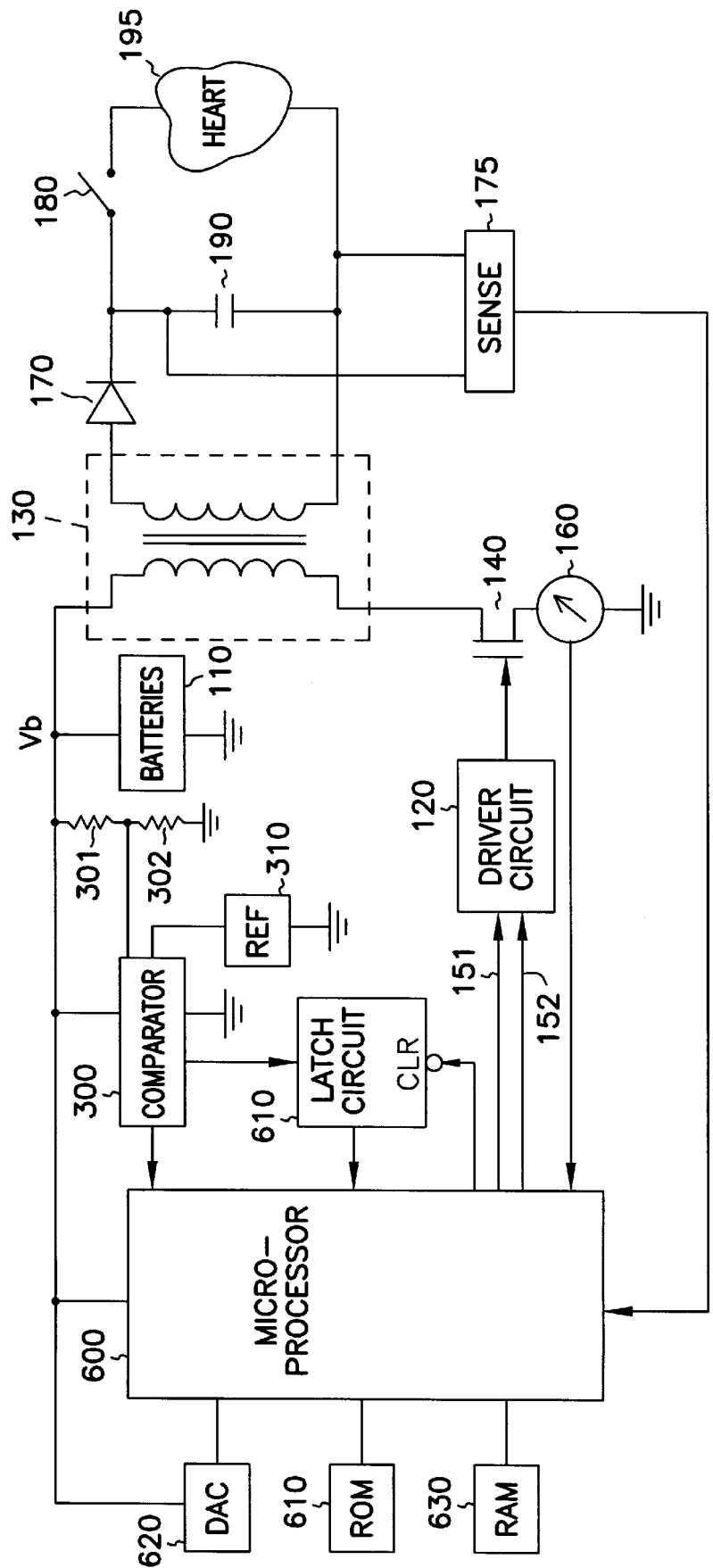
FIG. 6 is a block diagram of a microprocessor-based battery management system for a pulse delivery device according to one embodiment of the present invention.

FIG. 6 shows one embodiment of the present invention in which a microprocessor is used to monitor the output of comparator 300 and control the switch signal to switch 140 via driver circuit 120. This embodiment also includes a latch 610 to capture transitions of comparator 300. In one embodiment, microprocessor 600 performs a number of operations and only periodically polls the state of latch 610. In this embodiment, latch 610 serves as a memory of any transitions of the comparator 300 and frees microprocessor 600 to perform a variety of processing operations independent of the monitoring process. In another embodiment, the latch 610 is connected to an interrupt input on microprocessor 600 and serves to trap even a very short transition of comparator 300.

The addition of microprocessor 600 provides a means for intelligent management of the batteries 110. For example, the microprocessor is programmable to acquire information such as total charge time and nibbling information. Information acquired may be used to characterize the batteries' 110 as they age determine the depth of discharge of the batteries. A digital to analog voltage converter 620 converts the battery output voltage, Vb, into a digital representation. Other embodiments provide a connection to the voltage reference 310 to provide a relative measurement of battery output voltage to the voltage reference. RAM 630 and ROM 610 provide additional storage for microprocessor 600 and may be used to store conversion factors for relating the digital voltage representations from the DAC 620 to an absolute voltage value.

Charge Cycles and Nibbling

In one embodiment, microprocessor 600 is programmed to recognize whether "nibbling" occurs in a charge cycle, how much time the nibbling requires, the duration of the charge cycle, and at what point in the charge cycle the nibbling function is invoked. A charge cycle is the sequence of switching pulses needed to fully charge the output capacitor 190.

For purposes of demonstration the following discussion focuses on FIGS. 7A, 7B, and 7C, which are plots of the switch signal over the period of the charge cycle. As shown in FIG. 7A, when the batteries are new the entire charge cycle will complete without invoking the nibbling function and the output capacitor 190 is fully charged in time T.

FIG. 7B shows that as the batteries age the voltage delay effect causes an invocation of the nibbling function at the beginning of the charge cycle to "burn off" the transient resistance, as earlier described. This is termed "front end nibbling" since the nibbling function is invoked at the beginning of the charge cycle. A full charge cycle requires more time than when the batteries were new, since the nibbling extends the amount of time required to fully charge the output capacitor 190. This extra time is shown as ΔT in FIG. 7B. Therefore the total charge time in FIG. 7B to complete the charge cycle is T+ΔT.

FIG. 7C shows that as the batteries mature the nibbling function is invoked several times within a charge cycle. Since the charge cycle may be spread out over more time than a newer battery system, the pulses in FIG. 7C are not to scale with the pulses in FIGS. 7A and 7B. The pulses in FIG. 7C are shortened somewhat to illustrate the repeated invocation of the nibbling function over the charge cycle. The nibbling function will be invoked even after the transient resistance is initially "burned off", since the output voltage of the batteries during charging approaches the threshold voltage of the reference 310. If the batteries are not replaced the ultimate result for very aged batteries is invocation of the nibbling function through the very end of the charge cycle, since the closed circuit output voltage of the aged batteries will repeatedly be pulled below the threshold voltage as the output capacitor 190 is charged. This is called "back end nibbling," since the nibbling function is invoked to the very end of the charge cycle, as shown in FIG. 7C. A complete charge cycle requires more time to fully charge the output capacitor as the amount of nibbling increases. The extra time needed to fully charge the output capacitor is shown as ΔT' in FIG. 7C. Therefore the total charge time in FIG. 7C to complete the charge cycle is T+ΔT'.

One Embodiment of a Battery-Test System

In one embodiment of the present system, the battery management function includes a requirement to turn on a warning beeper when the open-circuit battery voltage reaches an elective replacement voltage. In one embodiment, a plurality of elective replacement voltages provide a highly programmable hierarchy of elective replacement events, which can be detected as the application demands.

For example, a single WGL 8513 battery as shown in FIG. 2, has a first elective replacement voltage, ERT1, which is approximately 2.45 volts and a second voltage, ERT2, which is approximately 2.2 volts. For systems where it is crucial to notify when the user of the battery powered device, the battery management system can be programmed to warn the user when ERT1 is reached to provide adequate time for replacing the device or its batteries. In a system where the notification is not as crucial, ERT2 may be used.

The ERT1 and ERT2 battery levels are determined by the open-circuit battery test. Other voltage levels of interest also determined by the open-circuit test are BOL1, BOL2, BOL3, MOL1, MOL2, and EOL.

In one embodiment, the device open-circuit battery test is automatically executed every 24 hours in field units. The test involves comparing a DAC value determined by the noise-compensation systems described here to predetermined DAC values, stored in a RAM DAC table. Each DAC value in the table represents a battery voltage of interest. The first value represents the highest voltage, BOL1, and each successive table value represents a lower voltage.

The battery test DAC value is determined by sampling the output of a comparator which is fed by the DAC voltage and the voltage-divided value of the open-circuit battery voltage (0.4 times the open-circuit battery voltage). The comparator outputs a logical one if the battery voltage is higher than the DAC voltage and a logical zero if the battery voltage is lower.

The device battery-test system is designed to compensate for two different environmental factors that can affect the outcome of the battery test. One of the factors is circuit noise that can affect the comparison between the open-circuit battery voltage and a given DAC value. If circuit noise exists and if a change in comparator sample time can occur within a given device, a voltage discrepancy can arise if the battery DAC trim values are determined when one phase of noise is at the comparator input and the opposite phase is present when the 24-hour battery test is run. The device battery-test system described here eliminates this discrepancy if the calibration procedure uses the same compensation system. The calibration procedure is not described here.

A second factor that can result in battery voltage variation is a change in ambient temperature. A battery test result that differs from a succeeding battery test result run 24 hours later may be due to a change in temperature rather than an actual lowering of battery voltage. This system incorporates a means to compensate for changes between 24 hour battery test results not due to battery depletion.

Figure 5B:
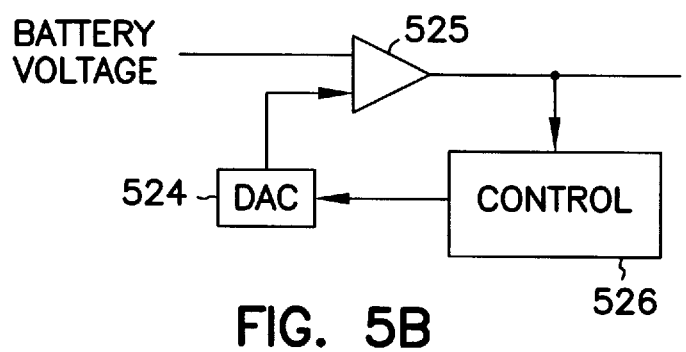
FIG. 5B is a block diagram of one example of a battery test circuit.

One system for battery test is described in the following two parts. The first part deals with the noise-compensation method. The second part deals with the temperature-compensation method. One example of a battery test circuit is shown in FIG. 5B. A DAC 524 provides a variable voltage input for comparator 525 under instructions from control 526. Outputs from comparator 525 are acquired by control 526 to determine if the voltage produced by DAC 524 is greater than or less than the battery voltage. Other variations are possible which do not depart from the present invention and this example is for demonstration and is not intended to be limiting or exclusive.

Part One: Noise Compensation

The general approach of this system is described as follows:

All DAC values starting with the first value in the table until the comparator output is a one are checked. For each DAC value the output of the comparator is read a predetermined number of times, here sixteen, in succession. The time between each reading is selected to ensure that the positive and negative extremes of the noise are sampled. By comparing all DAC values from, say, OE to 24 to the battery voltage, the voltage will be located between the DAC value where the comparator output is all zeros and the DAC value where the output is all ones.

As shown in the table below, a row of zeros indicates that the voltage is below the corresponding DAC value. The battery voltage shown below is between the voltages corresponding to DAC values 1B and 1E. For DAC values 1C and 1D, the ones and zeros indicate the voltage is fluctuating above and below each DAC value, corresponding to the noise signal.

| DAC value | Comparator output | | | | | | | | | | | | | | | | |
|---|---|---|---|---|---|---|---|---|---|---|---|---|---|---|---|---|---|
| 0E | 0 | 0 | 0 | 0 | 0 | 0 | 0 | 0 | 0 | 0 | 0 | 0 | 0 | 0 | 0 | 0 | |
| OF | 0 | 0 | 0 | 0 | 0 | 0 | 0 | 0 | 0 | 0 | 0 | 0 | 0 | 0 | 0 | 0 | |
| 10 | 0 | 0 | 0 | 0 | 0 | 0 | 0 | 0 | 0 | 0 | 0 | 0 | 0 | 0 | 0 | 0 | |
| 11 | 0 | 0 | 0 | 0 | 0 | 0 | 0 | 0 | 0 | 0 | 0 | 0 | 0 | 0 | 0 | 0 | |
| 12 | 0 | 0 | 0 | 0 | 0 | 0 | 0 | 0 | 0 | 0 | 0 | 0 | 0 | 0 | 0 | 0 | |
| 13 | 0 | 0 | 0 | 0 | 0 | 0 | 0 | 0 | 0 | 0 | 0 | 0 | 0 | 0 | 0 | 0 | |
| 14 | 0 | 0 | 0 | 0 | 0 | 0 | 0 | 0 | 0 | 0 | 0 | 0 | 0 | 0 | 0 | 0 | |
| 15 | 0 | 0 | 0 | 0 | 0 | 0 | 0 | 0 | 0 | 0 | 0 | 0 | 0 | 0 | 0 | 0 | |
| 16 | 0 | 0 | 0 | 0 | 0 | 0 | 0 | 0 | 0 | 0 | 0 | 0 | 0 | 0 | 0 | 0 | |
| 17 | 0 | 0 | 0 | 0 | 0 | 0 | 0 | 0 | 0 | 0 | 0 | 0 | 0 | 0 | 0 | 0 | |
| 18 | 0 | 0 | 0 | 0 | 0 | 0 | 0 | 0 | 0 | 0 | 0 | 0 | 0 | 0 | 0 | 0 | |
| 19 | 0 | 0 | 0 | 0 | 0 | 0 | 0 | 0 | 0 | 0 | 0 | 0 | 0 | 0 | 0 | 0 | |
| 1A | 0 | 0 | 0 | 0 | 0 | 0 | 0 | 0 | 0 | 0 | 0 | 0 | 0 | 0 | 0 | 0 | |
| 1B | 0 | 0 | 0 | 0 | 0 | 0 | 0 | 0 | 0 | 0 | 0 | 0 | 0 | 0 | 0 | 0 | |
| 1C | 0 | 0 | 0 | 0 | 0 | 1 | 0 | 0 | 0 | 0 | 1 | 1 | 0 | 0 | 0 | 0 | Battery voltage |
| 1D | 1 | 0 | 0 | 0 | 1 | 1 | 1 | 0 | 0 | 0 | 1 | 1 | 1 | 0 | 0 | 1 | is here |
| 1E | 1 | 1 | 1 | 1 | 1 | 1 | 1 | 1 | 1 | 1 | 1 | 1 | 1 | 1 | 1 | 1 | |
| 1F | 1 | 1 | 1 | 1 | 1 | 1 | 1 | 1 | 1 | 1 | 1 | 1 | 1 | 1 | 1 | 1 | |
| 20 | 1 | 1 | 1 | 1 | 1 | 1 | 1 | 1 | 1 | 1 | 1 | 1 | 1 | 1 | 1 | 1 | |
| 21 | 1 | 1 | 1 | 1 | 1 | 1 | 1 | 1 | 1 | 1 | 1 | 1 | 1 | 1 | 1 | 1 | |
| 22 | 1 | 1 | 1 | 1 | 1 | 1 | 1 | 1 | 1 | 1 | 1 | 1 | 1 | 1 | 1 | 1 | |
| 23 | 1 | 1 | 1 | 1 | 1 | 1 | 1 | 1 | 1 | 1 | 1 | 1 | 1 | 1 | 1 | 1 | |
| 24 | 1 | 1 | 1 | 1 | 1 | 1 | 1 | 1 | 1 | 1 | 1 | 1 | 1 | 1 | 1 | 1 | |

As the battery voltage slowly decreases rows of ones will be replaced by rows of ones and zeros, and ones and zeros will be replaced by all zeros. If the voltage was calibrated on the bottom of the noise signal, then the level of interest for a calibrated DAC value is when the output of the comparator changes from all ones to ones and zeros. If it was calibrated on the top of the noise, the level of interest is when the output changes from ones and zeros to all zeros.

Note that if the noise did not exist, the voltage would be determined by the DAC value when the comparator output changes from all ones to all zeros. There would be no rows of ones and zeros.

For any given DAC voltage below the battery voltage the comparator output will be all ones. As the battery voltage decreases below that value, the bottom of the noise will cause a row of all ones to change to ones and zeros. For example, to get a correct reading of the ERT1 battery voltage when this change occurs at the MOL2/ERT1 boundary, it is necessary to know if the voltage was calibrated on the top or bottom of the noise. If it was calibrated on the bottom, the battery voltage is at the ERT1 level when the change to ones and zeros (or to all zeros) occurs. If it was calibrated on the top, the voltage needs to decrease to the level when ones and zeros changes to all zeros. In all cases for a DAC value of interest, if the comparator output is all zeros the battery voltage is lower than that DAC voltage.

For this version of the battery test, it is assumed that calibration occurred using the bottom of any noise signal, and therefore, all battery levels will be determined using the DAC value that results in all ones, i.e., the OnesDAC.

After determining the OnesDAC, it is compared to the predetermined DAC values in the DAC table to determine the current battery status. If the status is a voltage greater than ERT the result is presented after a single battery test. However, if the result is ERT or lower the second part of this system is required before declaring an ERT.

Part One: Flow Chart Description

Figure 10:
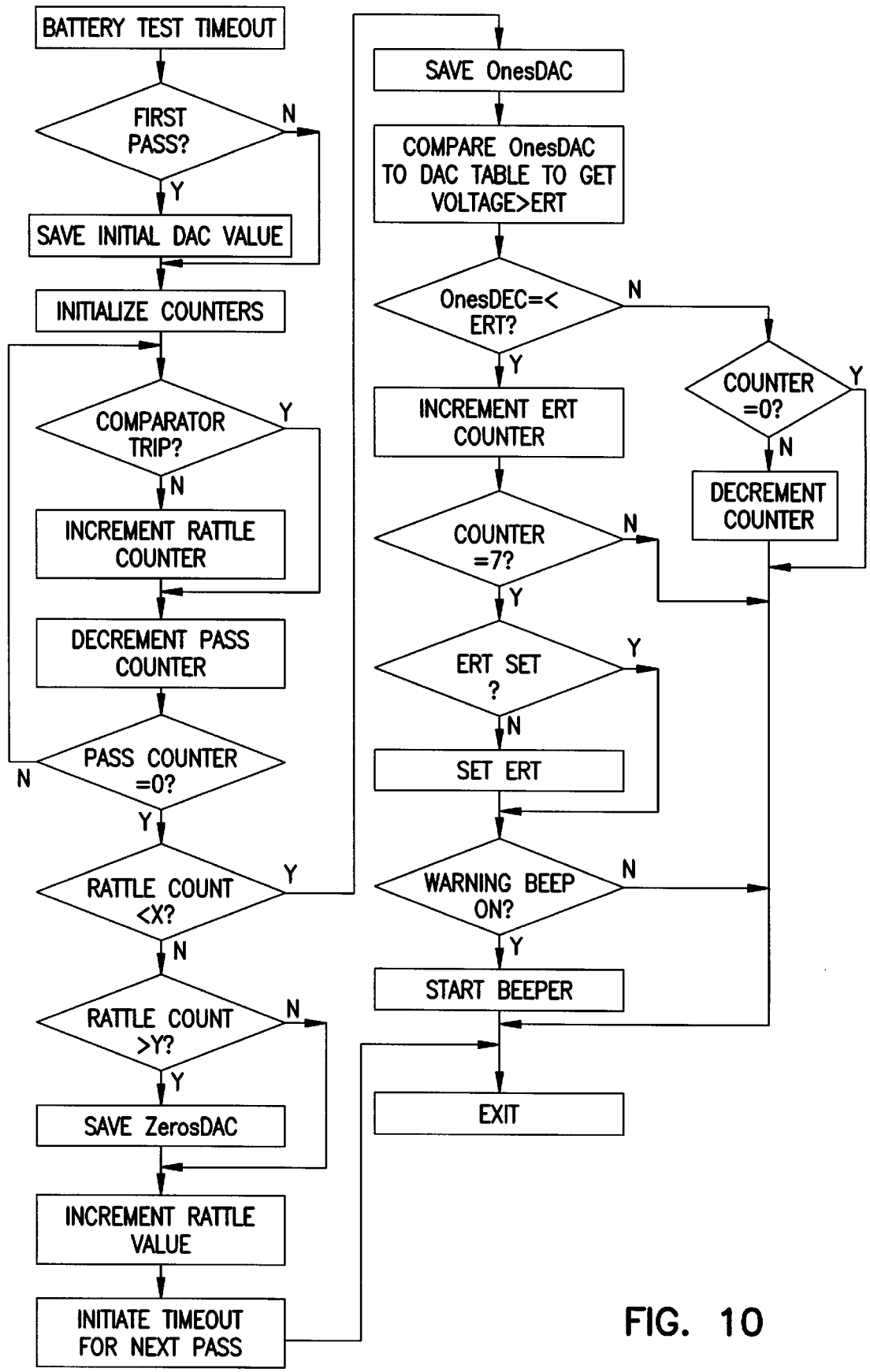
FIG. 10 is a flow chart of the voltage measurement system according to one embodiment of the present invention.

The particular operation of the compensation system, as shown in the flow diagram of FIG. 10, is as follows. The test starts by loading the BOL1 value into the device DAC. For the initial pass of the battery test the BOL1 value is saved as a potential system result, i.e., the battery voltage may be at the BOL1 level when the test is executed. At the start of each pass of the test counters, a pass counter and a rattle counter, are initialized.

The DAC voltage and the battery voltage are fed into a comparator circuit that outputs a logical one if the battery voltage is higher than the DAC voltage and a logical zero if the battery voltage is lower. If the comparator output is a one for the DAC value examined the pass counter is decremented. If the comparator output is a zero, the rattle counter is incremented before the pass counter is decremented. For each DAC value to be tested the comparison is made until the pass counter is decremented to zero.

If the rattle count is greater than a selected value the comparator output is considered a zero for the selected DAC value, and the next successive DAC value (DAC value+1) is examined. If the rattle count is less than a selected value the comparator output is considered a one and the DAC value is saved as the OnesDAC. This DAC value is used to compare to the DAC table values. The process continues until the comparator output is a one or until all DAC values have been examined. If the comparator output is still a zero when the last DAC value has been examined the battery is at EOL.

Part Two: Temperature Compensation

The second part of the system involves a method to compensate for differences between successive 24-hour battery tests that are not due to battery depletion. An up/down counter (ERT counter) is required to have a count of seven before ERT is declared. This part of the system works as follows:

After the OnesDAC is determined from the first part of the system, the OnesDAC is compared to the DAC value representing ERT. If the OnesDAC is less than or equal to the ERT value a counter, the ERT counter, is incremented. If the OnesDAC is greater than the ERT value the counter is decremented, unless it is already zero.

This comparison of a OnesDAC to the ERT value is made at every 24-hour battery test. If the ERT count reaches seven, ERT is declared.

Nibbler Operation

Figure 9:
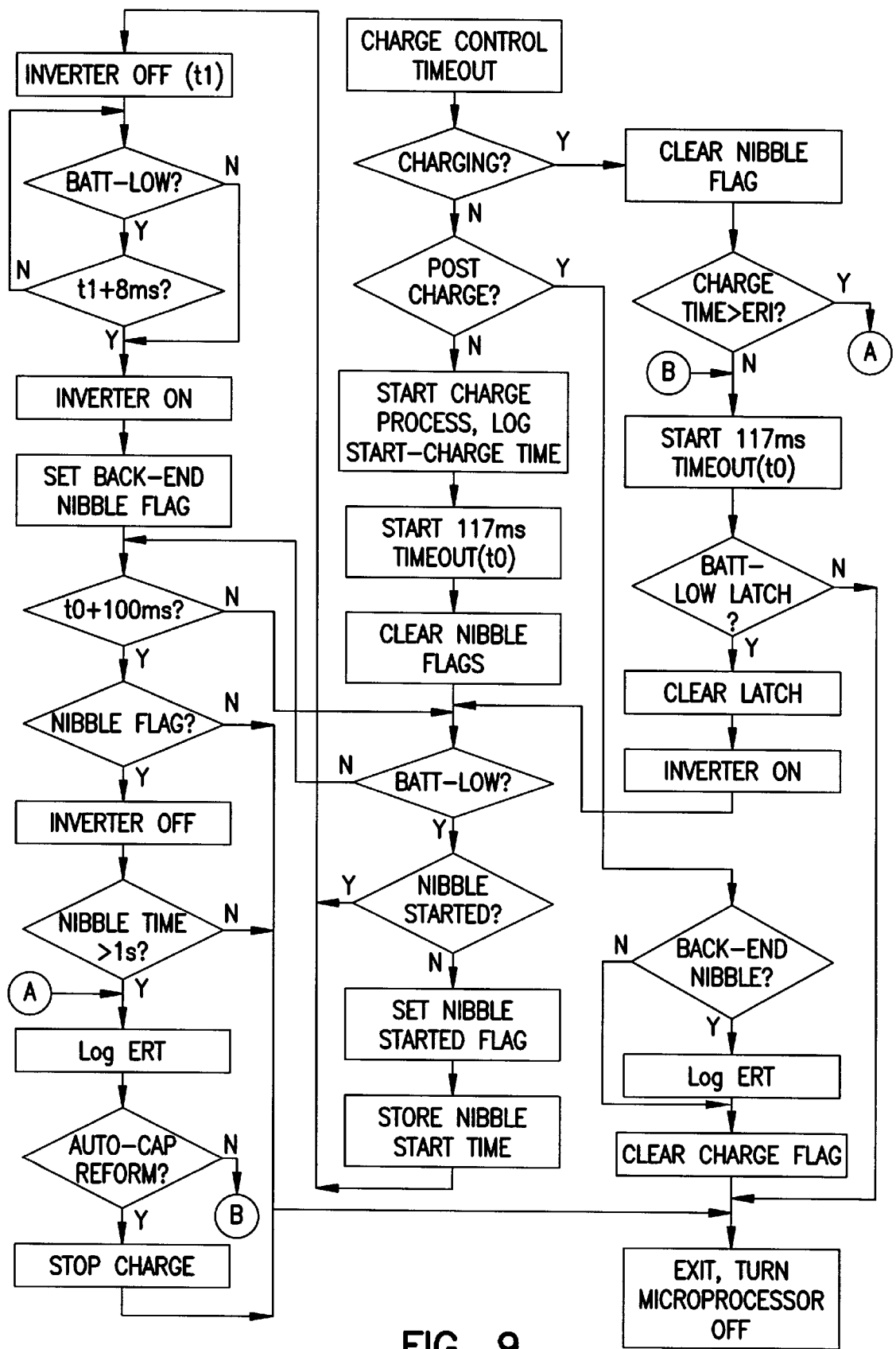
FIG. 9 is a flow diagram of the nibbler system according to one embodiment of the present invention.

The nibble function can be invoked at the start of any charge procedures and can operate throughout the charge cycle if necessary. One embodiment of the nibble function is illustrated in the flow diagram shown in FIG. 9.

A charge process is initiated in the ROM 610 code by loading a value into a charge-control DAC 620. The sense circuit 175 limits the capacitor voltage to the value selected for the given charge. After loading the DAC 620 with a delay, the charge control timeout (117 msec), is initiated. When the delay times out, control of the charge procedure is relayed to the nibbler program located in RAM 630.

When the initial charge control timeout occurs, the inverter 130 is turned on to start the charging process and the start-charge time is stored. Nibble flags are initialized and another timeout of 117 msec is initiated. After the initial timeout the microprocessor 600 is kept running for the next 100 msec to monitor the batt-low signal from comparator 300 (the signal indicating that the supply voltage has fallen below the threshold voltage set by voltage reference 310). The 117 msec timeout will be repeated throughout the charging procedure, but after the first charge-control timeout the 100 msec period occurs only when a batt-low condition occurs.

If a batt-low occurs while the microprocessor 600 is running, a nibble flag is set and the inverter is turned off. The time for the first occurrence of a batt-low condition is stored as the nibble start-time. The nibble start time can be compared to the start-charge time at a later time, e.g., after programmer interrogation, to determine if nibbling occurred at the start of the charge cycle.

After turning the inverter 130 off monitoring of the batt-low signal is continued, and when the battery voltage rises above the batt-low level the inverter 130 is turned back on. The inverter turn-off/turn-on (nibbling) process will be repeated throughout the initial 100 msec of the charging cycle as long as a batt-low occurs.

If a batt-low does not occur during the 100 msec period, the inverter 130 will not be turned off during this period. At the end of the 100 msec the microprocessor 600 will be turned off. If a batt-low has occurred the inverter 130 will also be turned off; if a batt-low has not occurred the inverter 130 will be left on.

When the microprocessor 600 is turned back on ~17 msec after the end of the initial 100 msec period, control is again relayed to the nibbler system. At this timeout and every 117 msec timeout thereafter during the charge procedure the charge time is checked. If the charge time exceeds a programmable time (e.g. 32 seconds), ERT2 is declared. Charging for a manual or automatic capacitor reform is not allowed to exceed 32 seconds and in the event charging for either of these reaches 32 seconds the charging is terminated. However, charging for therapy charging continues until completed.

If the current charge time is less than the ERT2 time, another timeout is initiated and the batt-low latch 610 is checked. The batt-low latch 610 will be set any time a batt-low signal has occurred. If the latch is set it is then cleared and the inverter 130 is turned on.

If a batt-low has occurred during the previous period, as indicated by the presence of a latched batt-low, the microprocessor 600 will be kept running for the next 100 msec to monitor the batt-low signal. The nibbling process will be repeated during the 100 msec period as long as a batt-low occurs. If a batt-low latch signal is not present at this time, indicating that nibbling did not occur in the previous 100 msec period, there will be no 100 msec monitoring period. The microprocessor 600 will be turned off but the inverter 130 will be left on. The next wakeup for monitoring batt-low will be in 117 msec.

Anytime the microprocessor 600 is kept running for 100 msec due to a batt-low, the inverter 130 will be turned off when the microprocessor 600 is turned off at the end of the 100 msec period. If there is no 100 msec microprocessor turn-on period, the inverter 130 is left on throughout the charge.

At the end of a 100 msec nibble period, the nibble time is checked. If the nibble time exceeds one second, ERT2 is declared. If the capacitors 190 are being charged for autoreforming, the charge process is terminated. Otherwise, charging continues until completed.

At the completion of a charge cycle a check for back-end nibbling is made. Back-end nibbling is defined as nibbling that is ongoing at the time the capacitors reach the charged state. ERT2 is declared anytime nibbling occurs at the end of a charge cycle.

The charging of the high voltage capacitors, when a battery-low condition occurs during charging, will be maintained by the process of turning the inverter 130 circuit off when a battery-low occurs and turning the inverter 130 back on when the battery-low goes away. This process is referred to as nibbling, and the process will operate during the charge cycle as long as a battery-low occurs, throughout an entire charge cycle if necessary.

In one embodiment, ERT2 is declared when any charge reaches 32 seconds in duration (programmable). Charging for either a manual or automatic reform procedure will not be allowed to exceed 32 seconds. ERT2 is declared when nibbling occurs and exceeds one second in duration. Automatic capacitor reforms will be terminated if nibbling reaches one second in duration. Additionally, ERT2 is declared if back-end nibbling occurs during any charge cycle. Other variations are possible without departing from the scope and spirit of the present invention.

An Advanced Power Management System

Figure 8A:
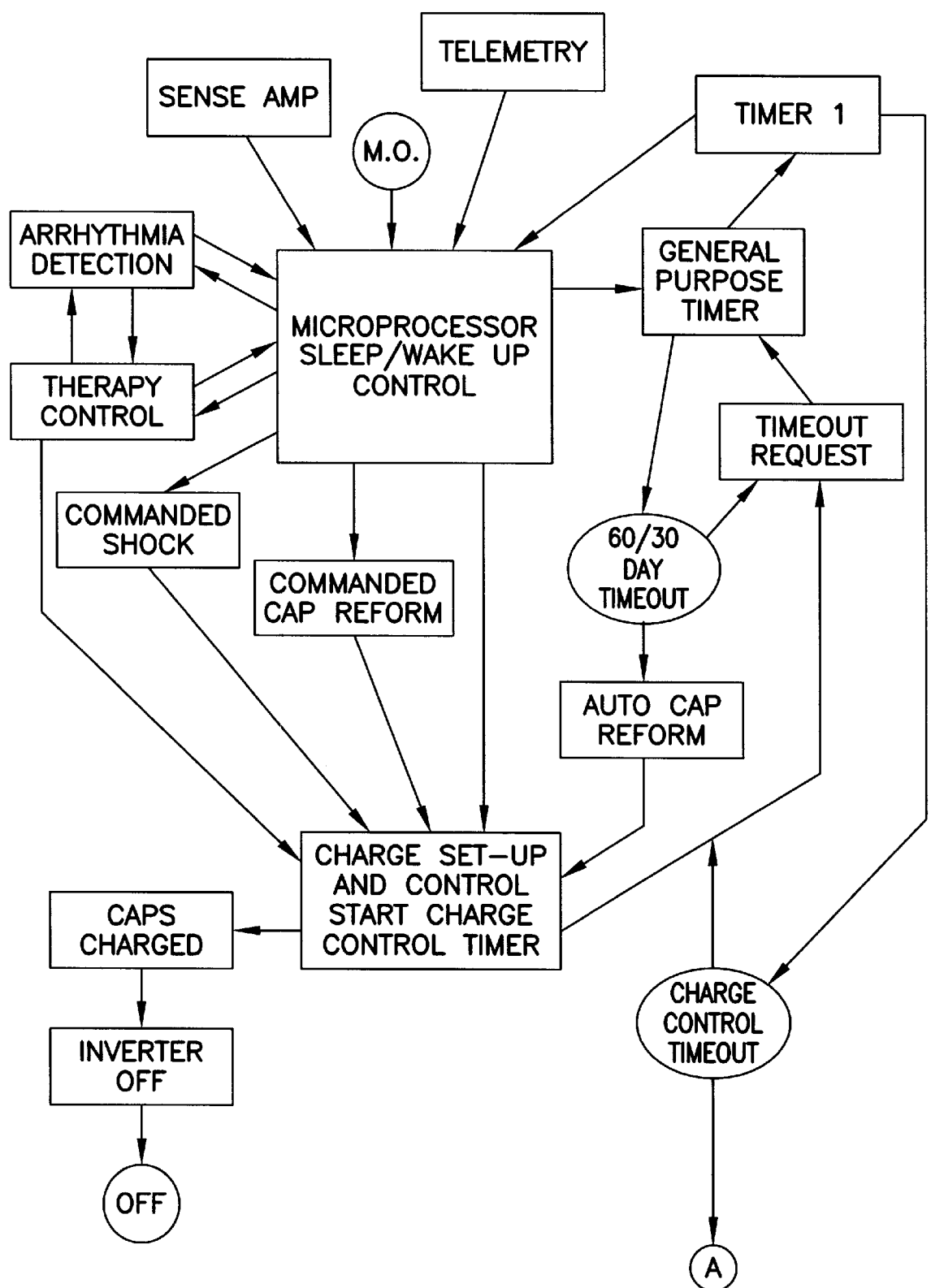
FIG. 8A and FIG. 8B are flow diagrams demonstrating an advanced battery management system according to one embodiment of the present invention.
Figure 8B:
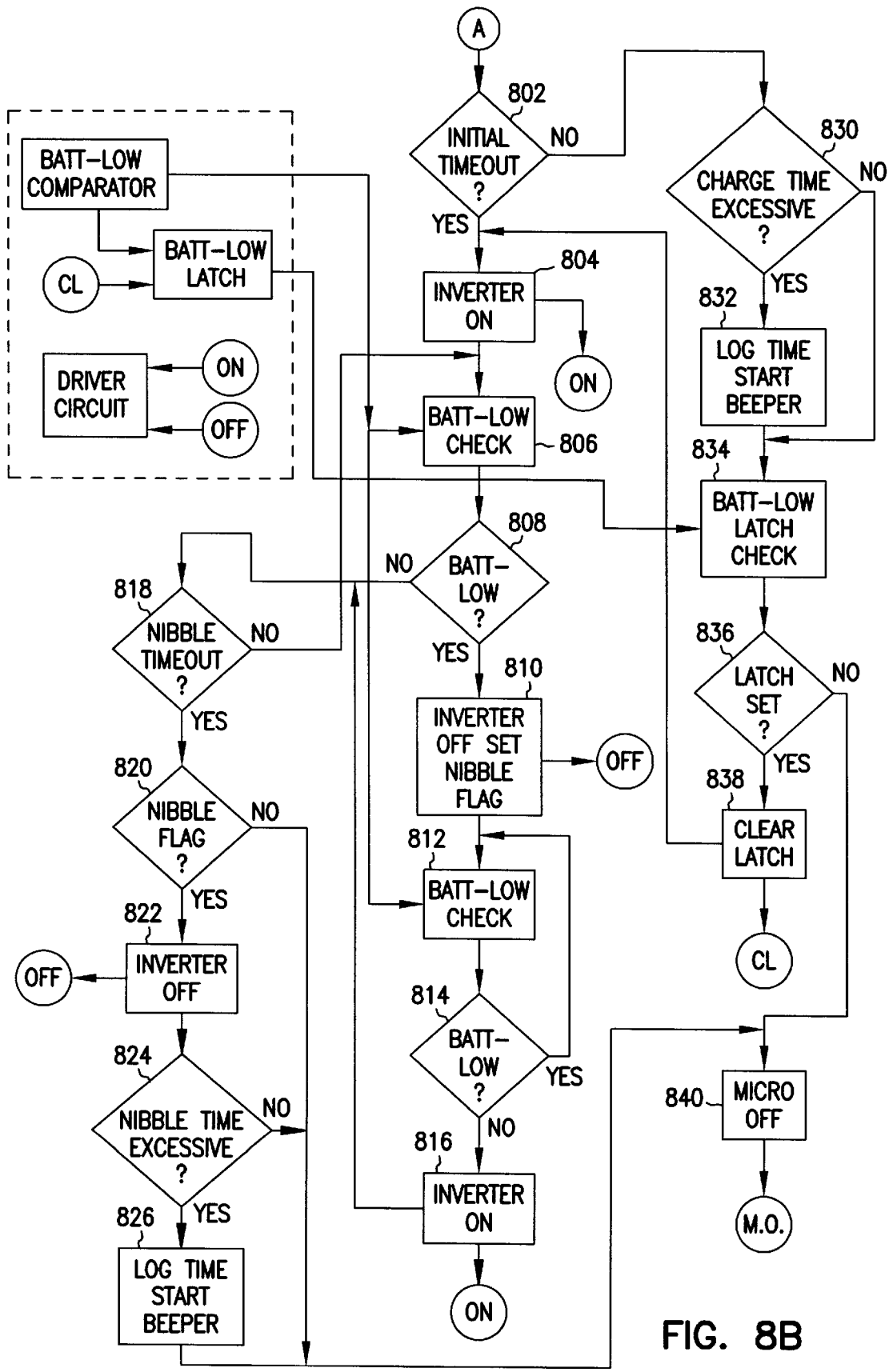

FIG. 8 shows a flow diagram of one embodiment an advanced power management system where the processor performs a number of processing functions, including arrhythmia detection, shock, capacitor reform, telemetry and timing. The microprocessor 600 is free to perform the variety of tasks as long as it provides adequate monitoring of the comparator 300 and the latch 610.

In this embodiment the microprocessor 600 polls the latch 610 and comparator 300 every 120 milliseconds. The time between polling events described herein is to demonstrate this embodiment of the present system and is not intended in an exclusive or limiting sense. The time between polling may be reduced to provide more resolution to the sampling of the battery output voltage.

If the system is performing the first polling of the nibbling hardware 802 then the inverter is turned on 804 and comparator 300 is checked to see if the battery voltage is below the threshold voltage 806. If the battery voltage is below the threshold voltage then the inverter is deactivated 808, 810 to perform the requisite nibbling function. The voltage check is performed continuously until the battery voltage exceeds the threshold voltage 812, 814, whereupon the inverter is again activated 816. If the nibble time exceeds 100 milliseconds 818 then nibble flag 820 is set and the inverter is turned off 822 and the total nibble time is checked to determine if it exceeds 1 second 824 in which case ERI is declared and a beeper is activated to alert the patient 826.

If the system is performing a subsequent polling of the nibbling hardware 802 then if the charge cycle time exceeds 1 second 830 then ERT is declared and a beeper is sounded to alert the patient 832. If the charge cycle time is not excessive then the latch 610 is checked 834 and if it is not set then no nibbling is necessary and the microprocessor 600 can perform other functions or go back to sleep 840. If the latch 610 is set then nibbling is necessary, since the battery voltage dropped below the threshold voltage. The latch 610 is cleared 838 and the nibbler routine as described above is entered to perform nibbling as needed (804–840, as above).

This highly efficient nibbling system provides a minimal interruption to the overall charge cycle time, while simultaneously greatly extending the usable lifetime of the batteries in the power supply.

An Alternate Embodiment of A Power Management System

Figure 12:
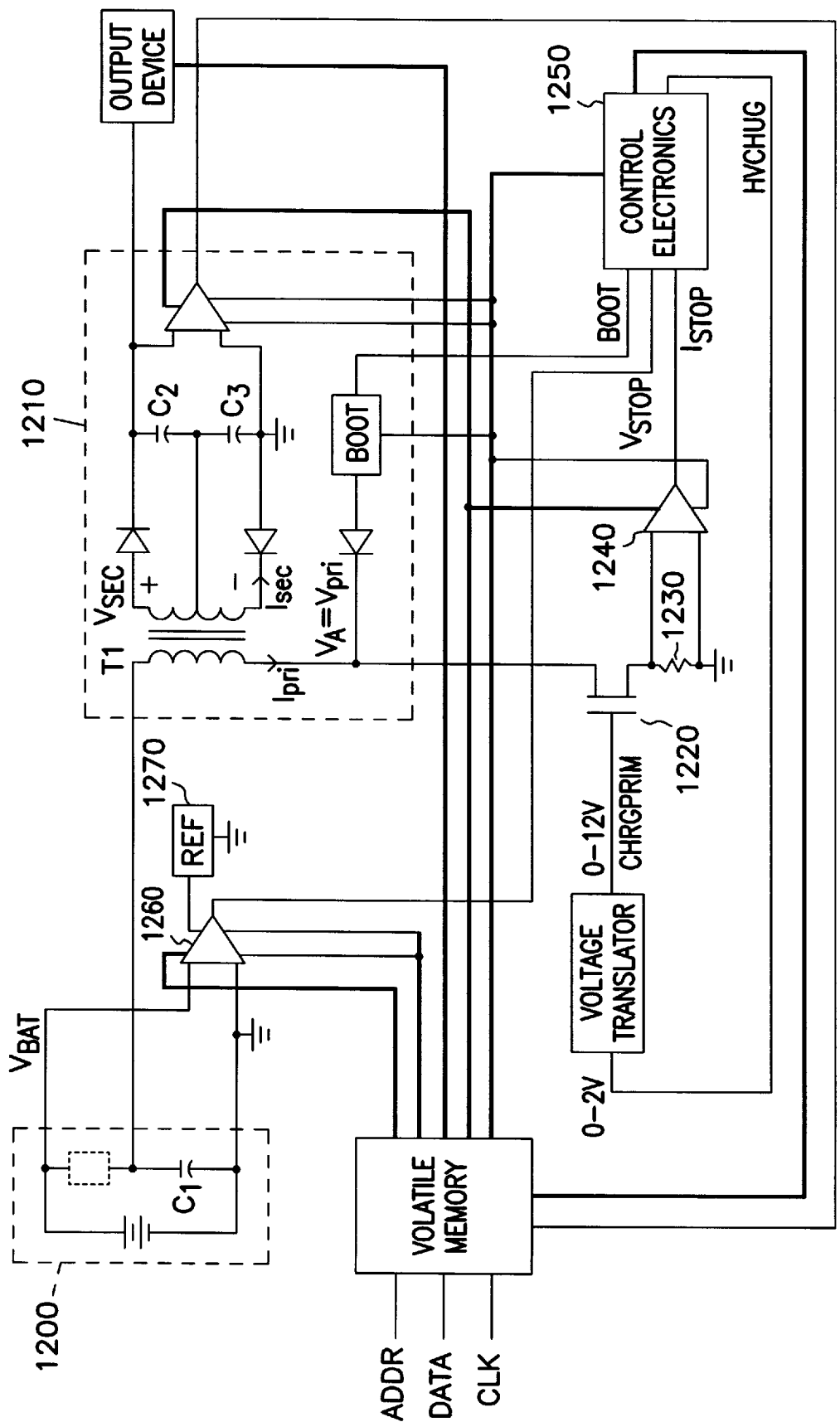
FIG. 12 is a logical block and schematic diagram of a voltage pulse generating system according to the present invention.

In this embodiment hardware is dedicated for both current control and monitoring the battery voltage to ensure proper charging of the output circuit and that the battery voltage does not fall below the reset voltage of the electronics. FIG. 12 shows one embodiment where control of the charging functions is performed in with a relatively short sampling time to inhibit the charging function within a single inverter pulse period. Such a design is especially useful for single battery systems, since the relatively short sampling time provides better control of battery voltage variation about a predetermined threshold voltage. However, this embodiment is not restricted to single battery systems.

FIG. 12 shows a block diagram of one embodiment wherein the current through the primary winding of the charging circuit 1210 is controlled by switch 1220 and monitored by current monitor 1230. Current comparator 1240 receives a voltage signal from current monitor 1230 to terminate a charge pulse applied to switch 1220 by control electronics 1250. An alternative control is provided by comparator 1260 which monitors the voltage on the battery 1200, Vbat, and compares it to a predetermined reference voltage 1270. If the charging cycle results in a Vbat below the reference voltage, then the charging is inhibited substantially as soon as the electronics in the control loop can respond.

In an alternate embodiment, the threshold voltage is a multiple of the reference voltage. For example, if the threshold voltage is 3.00 volts and the reference voltage is 1.5 volts, then Vbat is voltage-divided to one half its value to make the comparison. If this were not done, the fact that the system voltage, Vbat, potentially drops below the threshold voltage, would yield unpredictable results in both the reference supply 1270 and the comparator 1260 output.

Figure 18A:
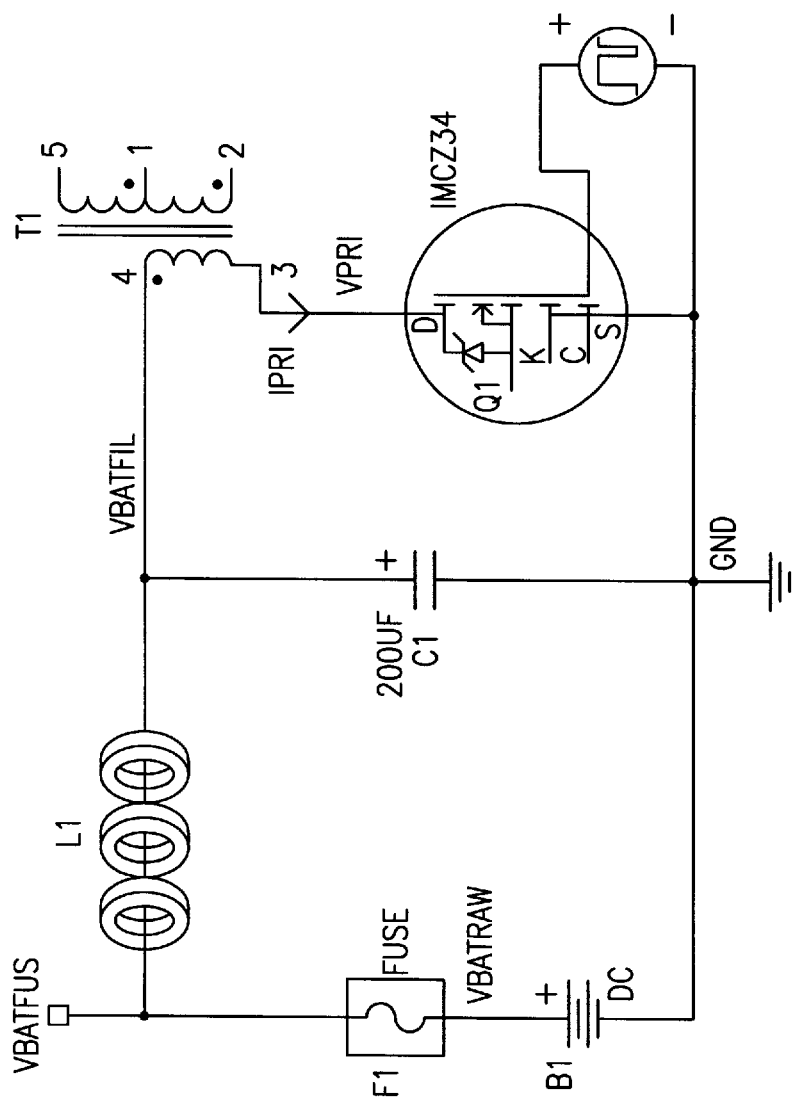
FIG. 18A is a schematic diagram of a BATLOW circuit for the voltage pulse generating system according to the present invention.
Figure 18B:
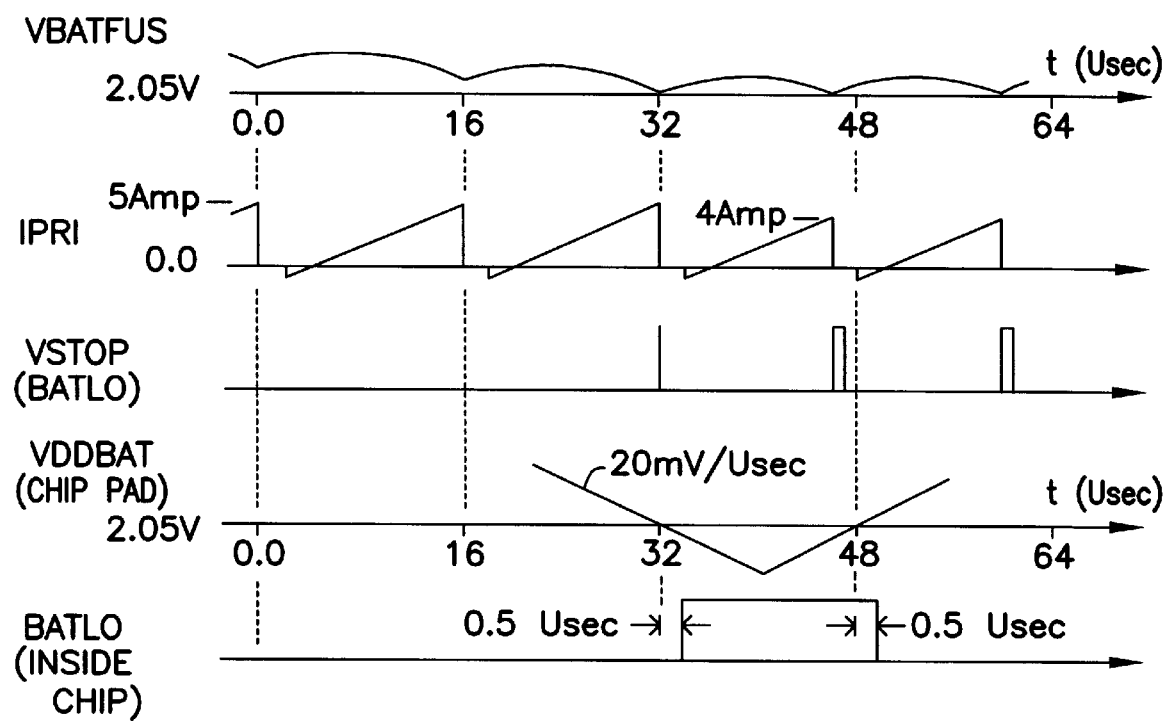
FIG. 18B is a timing diagram illustrating BATLOW System Waveforms and Test for the voltage pulse generating system according to the present invention.

If high speed electronics are used, the control loop will have the capability to nibble individual charge pulses and provides the type of pulse waveform control which approximates the idealized control in FIG. 4D and FIG. 18B. In one embodiment, control electronics 1250 includes a timer which is used as a backup limitation on the charging pulse duration. In another embodiment, the pulse train for charging the output circuit is a self-oscillating circuit. The pulses are initiated by a charge request and the pulses are terminated by reaching a current maximum, voltage nibbling, or by receiving a signal indicating a fully charged output circuit. The pulses are self-oscillating because as the transformer dumps its energy into the output circuit a "ringback" signal triggers the beginning of the next pulse. This allows the self-oscillating circuit to charge without a synchronous clock constraint and provides optimal charging times for the given nibbling feature. The self-oscillating embodiment and ringback detection system are described in greater detail below.

Each pulse to switch 1220 is named a "chug", since it provides the necessary time varying input to charging circuit 1210. The following is a detailed description of this embodiment of a real time current and voltage control power management system for an implantable device.

High Voltage System

The basic operation of the high voltage charge circuit is to store energy in the flyback transformer by building up flux by increasing the current through the primary, then cutting off the current in the primary which releases the stored energy by causing the flux to produce the high voltage. This basic operation just described is named as a "chug", and takes about 16 $\mu$sec to complete, in one embodiment.

In one embodiment, the high voltage supply is a switched mode, DC to DC flyback voltage converter. The purpose of this supply is to convert power from the battery 1200 (at approximately 2.5 V, 2 amps for about 9 seconds while charging) to energy stored in the shocking capacitors (700 V in 125 $\mu$f effective, or about 30J stored) for use in defibrillation therapy. The high voltage supply, shown in FIG. 13, consists of:

- a power transformer,
- a power sensefet,
- a current sense resistor,
- output capacitors,
- blocking diodes,
- output sense resistors, and
- an integrated control circuit.

The integrated control circuit consists of:

- a sensefet drive circuit,
- a peak current detect circuit,
- flyback detect circuit,
- a battery level detect circuit,
- an output voltage detect circuit, and
- digital control circuits.

The high voltage is supplied through the use of the flyback transformer as a means of voltage multiplication. The primary winding is charged across the battery until a programmed peak current is reached, or until a maximum "on" time is reached. During this charge interval, energy is stored in the transformer core in the form of magnetic flux. At the end of the charge interval, sensefet 1220 in the primary circuit opens and the energy stored in the core couples to the secondary winding. The voltage in the secondaries will rise until the rectifier diodes become forward biased; the energy contained in the core of the transformer as magnetic flux can now flow as (current*voltage) into the shock capacitors C2 and C3. This is known as the transfer interval.

When the current in the secondary winding drops to a level such that the secondary blocking diodes turn off, the energy remaining in the parasitic capacitance of the secondary circuit is reflected back to the primary where it is detected as a voltage ring (ringback) on the drain of the switch 1220 and is used to begin the next charge of the primary winding (the next "chug"). This type of operation is referred to as synchronous mode and occurs after the output voltage reaches a level which will cause the ringback voltage to be detectable. The present system has an alternate operating mode called asynchronous mode.

During the asynchronous operation the switching frequency of the sensefet is determined by the energy transfer rate and is operating asynchronous to the system clock. Before the asynchronous mode occurs, the circuit runs in a synchronous mode where the charge and transfer times of the circuit are controlled by the digital control circuitry and events are synchronous with the main system clock. The asynchronous mode of operation is more desirable since the natural frequency of the switcher is abut 100 KHz whereas the synchronous mode operates at the system clock of 32 KHz. Thus asynchronous mode results in shorter charge times since it operates at a higher switching frequency.

Charge Current

The high voltage charging circuit controls the amount of current flowing in the primary coil during the sensefet 1220 "on" time by monitoring a fraction of the primary current and shutting the sensefet 1220 "off" when a certain value of peak current is reached. If the circuit were untrimmed, the value of peak current would vary over an unacceptable range due to variances in sensefet sense ratio, transformer characteristics, circuit offsets and other variables. Measuring the actual peak value of current is a difficult problem under dynamic operation and average current was deemed to be a beneficial alternative. Also, since there is a capacitor across the battery, the current out of the battery is an averaged value of the actual primary current.

Operation near 2 V Battery Voltage

As the battery ages, the current pulled by the high voltage switcher will cause the battery terminal voltage to drop to lower and lower voltages. To avoid voltages low enough to cause system problems, a circuit is in place to detect the battery voltage and prevent the switcher from pulling it below a preset value. The circuit accomplishes this by ending the primary charge cycle before peak current is reached if the battery terminal falls near 2V. This will cause a transfer to secondary to occur and the next primary charge is prevented from beginning until the battery voltage recovers to an acceptable level. This results in less energy being transferred to the secondary on each chug. The end result is that the total charge time increases as the battery ages and can be used as an indication of battery condition.

T1 Transformer

Figure 13:
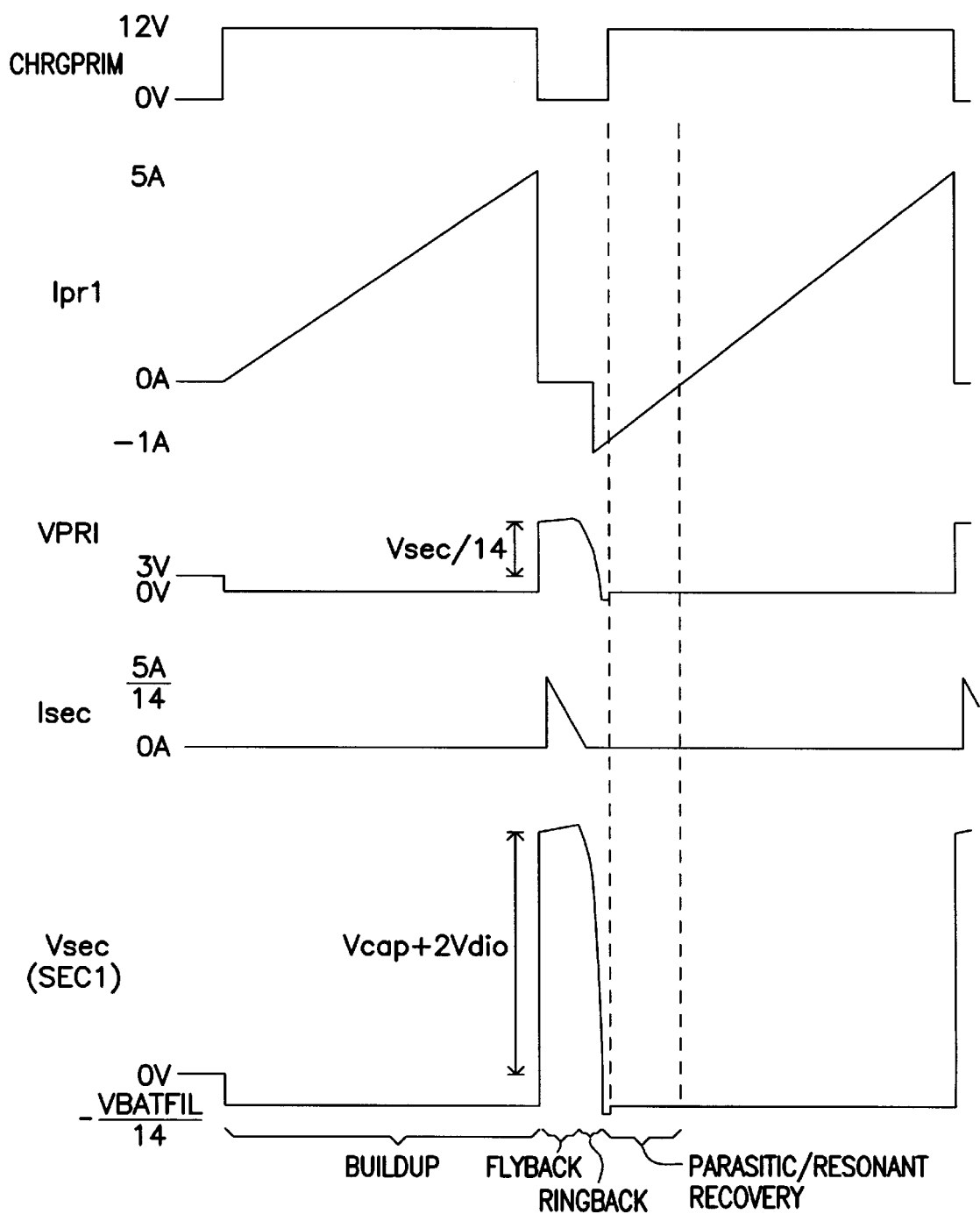
FIG. 13 is a timing diagram of current and voltage waveforms of a transformer for the voltage pulse generating system of the present invention.

A typical cycle ("chug") of the transformer is shown in FIG. 13; what follows in this section is a description of this operation.

The ferrite device that has been referred to here as "flyback transformer" T1 really functions as an intermittent energy storage device rather than as a continuous energy transfer device, as most transformers are used. The transformer law (such as Vout=n times Vin, where n is the turns ratio), will of course still apply, since they depend upon fundamental physical relationships connecting the magnetic flux in the core to the ampere-turns flowing in the primary and the secondary. The transformer has a primary winding consisting of 8 bi-filar turns and each secondary consists of 56 turns of single strand.

FIG. 13 shows typical waveforms involved in the operation of the transformer in the high voltage power supply. The signal CHRGPRIM is the gate signal of the sensefet and not actually a signal on the transformer. However it does serve to show the timing of the signals shown. The following are the remaining signals and a description of the signal:

Ipri current in the transformer primary;

Vpri voltage across the transformer primary;

Isec current in the transformer secondary; and

Vsec voltage across the transformer secondary.

In FIG. 13 the primary and secondary waveforms are not to the proper scale: they are 4:1 on the diagram, and in real life they are 14:1. The times, however, are of roughly correct scaling, and the proportions within waves are approximately correct.

Buildup Portion

A cycle begins by connecting the primary of the transformer across the battery, whose voltage is typically 2.5 to 3.0V at beginning of life; this connection is made by turning on switch 1220. Current Ipri begins to build up in the primary winding during this portion of the cycle (the buildup portion) in roughly a linear manner according to the law for linear inductances $$(di/dt)=(V/L)$$

where L is Lp, the primary inductance (6.25 $\mu$H, nominal), and V is the voltage across the bypass capacitor C1 (2.5V nominal). The actual current wave form will deviate somewhat from the true linear waveform because of the unavoidable resistances in the primary circuit, and in fact will be an exponential waveform. the resistance in the primary circuit comes from the on-resistance of switch 1220 (77 m$\Omega$), bypass capacitor C1's equivalent-series-resistance (35 m$\Omega$), transformer primary-resistance (20 m$\Omega$), and wiring interconnect-resistance (10 m$\Omega$), for total of 142 m$\Omega$.

This portion of the cycle ordinarily ends when the current in the primary reaches the peak value Ipk (this generates the internal signal ISTOP), which is trimmed so as to give an average current from the battery of 2.0 amps. Other appropriate, but extraordinary, end-of-cycle causes are BAT-TLO (VSTOP), INHIBIT, SYNC_CHUG, and LONGCHUG, as described below.

Flyback Portion

The next portion of a chug cycle (the flyback portion), is initiated by turning off the primary switch 1220, due to one of the causes indicated in the previous paragraph. Since the magnetic flux induced in the core of transformer T1 cannot instantaneously, some other current path must be found; this other current path will eventually (after various primary and secondary parasitic capacitances are charged up) be current through the rectifier diodes into the main defibrillator capacitors C2 and C3. The voltage across the secondary will initially be whatever it takes to maintain the flux in the transformer core (the voltage across the series combination of C2 and C3, plus two forward diode drops from the rectifier diodes), and the rest of the state variables of the transformer are inferred form the transformer laws $$Vpri=Vsec/n$$

and $$Isec=Ipri/n,$$

where n is the turns ratio from secondary to primary, in this embodiment, 14. Thus the initial primary voltage, when the secondary begins dumping current through the rectifier diodes, is given by $$Vpri=Vsec/14,$$

and the initial secondary current, when the secondary begins dumping current, is given by $$Isec=(Ipk/14).$$

As a specific example, near the end of a maximum shock energy charge sequence, and the secondary voltage is nearly 700V, the reflected primary voltage will be 50V and the initial secondary current will be 0.357 amps (assuming that a peak current for Ipk of roughly 5 amps is needed to obtain a average current out of the battery of 2.0 amps).

To obtain the current waveform in the secondary, the law for linear inductances $$(di/dt)=(V/L)$$

is again invoked, only this time the secondary inductance Ls (n times n times Lp, or 1.225 mH) is used instead of Lp, and Vs (the voltage across C2 and C3) is the appropriate voltage to be used. This linearly decaying ramp indicates the transfer of the energy stored as flux in the transformer core during the buildup portion of the cycle to the output capacitors C2 and C3. Recall that the energy is an inductor is given by $$E=(\tfrac{1}{2})L*I*I$$

The output capacitors C2 and C3 exhibit an increase in voltage due to the energy transferred to them according to the energy law for linear capacitors $$(\tfrac{1}{2})C(V_f*V_f-V_i*V_i)$$

where $V_f$ is the voltage on the capacitor after the energy transfer, and $V_i$ is the voltage on the capacitor before the energy transfer.

Ringback Portion

The third portion of a chug cycle (called the ringback portion), occurs between the time that the secondary current goes to zero and the time that the primary and secondary voltages go to zero. When the secondary current ramp reaches zero at the end of the flyback portion of the chug cycle, the energy in the transformer is zero since no current flows in either the primary or the secondary, and thus no current is flowing through the rectifier diodes. Not all the energy that was initially stored in the transformer T1, at the time that switch 1220 was turned off, is transferred to the output capacitors C2 and C3; some of the energy remains stored in the primary parasitic in the output capacitance of switch 1220, and in the dominant parasitic capacitances in the secondary (the capacitances associated with the rectifier diodes). These capacitances are of course coupled by the transformer T1, and form a resonant circuit with the transformer's inductance; the voltage across the primary moves from the value it sustained during the flyback portion of the cycle to zero in a sinusoidal waveform, the quarter period of which may be determined by the resonant circuit formed by the parasitic primary and secondary capacitances and the transformer inductance.

It is important to note that when the primary and secondary voltages go to zero during this portion of the cycle, some flux has been returned to the transformer core by currents that have built up in the inductances portion of the resonant circuit, and this current will tend to continue the voltage sinusoid across both the primary and secondary of the transformer T1. This negative swing has two important consequences. First, as the primary voltage goes approximately 1V negative with respect to the battery voltage, the signal called DBOOT is created; this is the signal that is used by the HV_CHUGGER circuit to initiate another chug cycle. Second, as the primary voltage continues to below ground it will eventually turn on the internal diode in switch 1220 (switch 1220 is a sensefet). The energy in the resonant circuit gets transferred back into the bypass capacitor C1; since the current is flowing into the bypass, it shows up on FIG. 13 as a negative current in Ipri (estimated to be about 1 amp).

Resonant/Parasitic Recovery Portion

The current that flows back into the bypass capacitor C1 from the energy in the resonant circuit can again be determined by the linear inductance equation $$(di/dt)=(V/L)$$

where V is the battery voltage plus the voltage drop due to the internal diode in switch 1220. L is again the primary inductance, and the initial condition on the current is the value of current in the primary necessary to sustain the flux that has been returned to the inductor from the parasitic capacitors through the means of the resonant circuit.

Chug Control

The HV_CHUGGER was designed to make it easy to stop a chug operation at any time during the primary build-up.

Boot

One of the ways that some assurance is obtained that all the flux is gone from the transformer core is to observe the primary voltage of the transformer. When the primary current is initially interrupted, the primary voltage rises to a voltage above the battery voltage given by the voltage across the secondary divided by the turns ratio or about 50V when the secondary voltage is 700V. When the secondary current has fallen to zero, the secondary voltage still present on the rectifier diode's depletion capacitance represents energy that will result in the primary voltage going below the battery voltage (in fact it will, for sufficiently large secondary voltages—say 50V—go below ground and cause the sensefet 1220 substrate diode to conduct). By observing and remembering the negative transition of the primary voltage, it becomes possible to start the next primary build-up only after the flux has been exhausted. This primary signal is called VPRI.

Figure 19A:
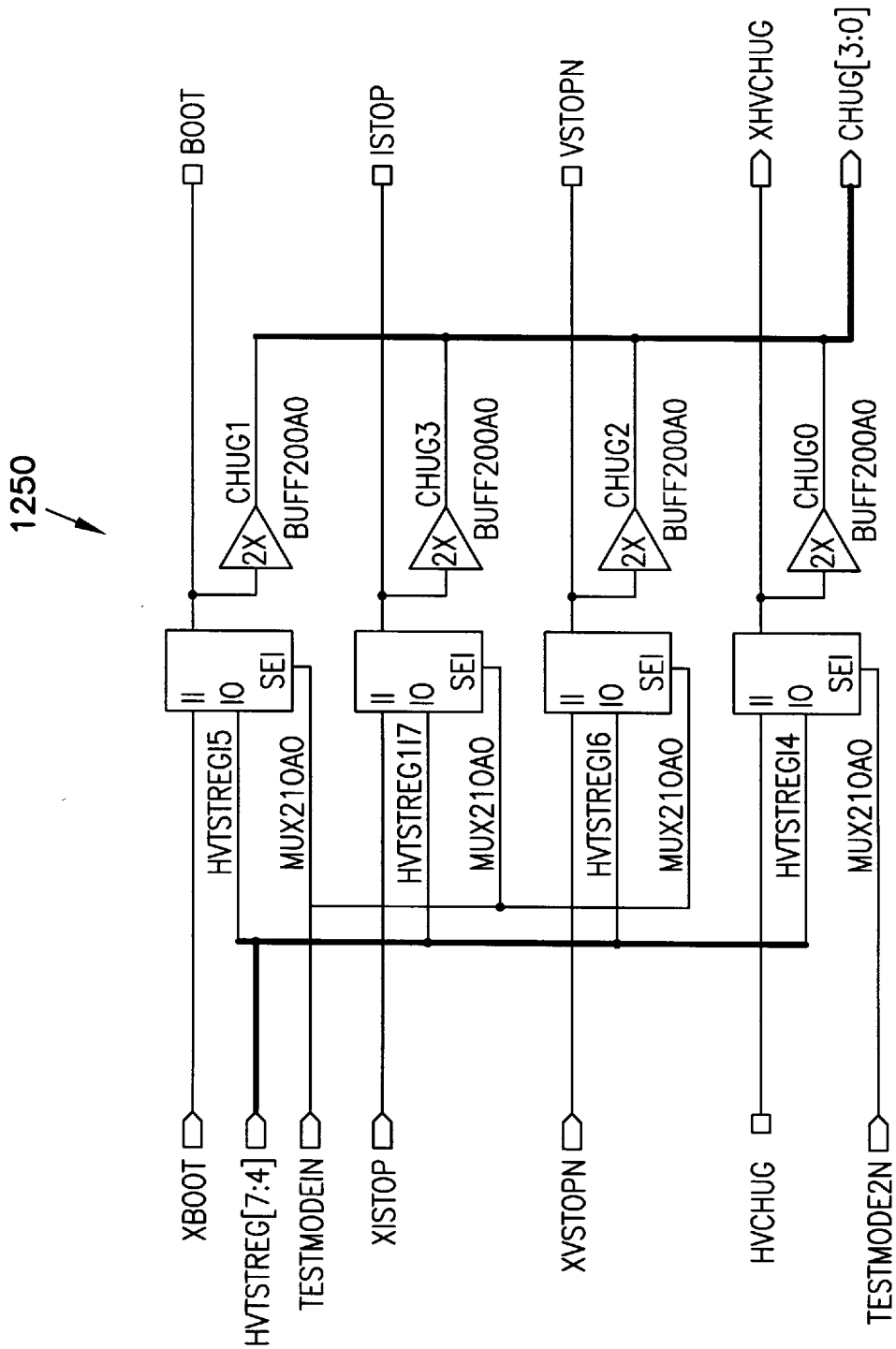
FIG. 19 is a logical block and schematic diagram of the "HV_CHUGGER" Circuit for the voltage pulse generating system according to the present invention.
Figure 19B:
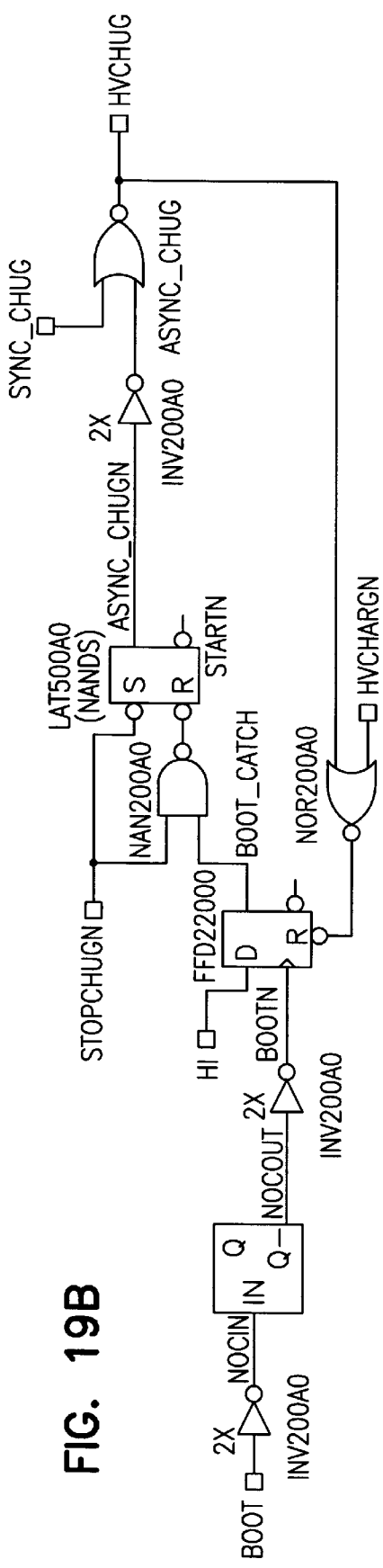
Figure 19C:
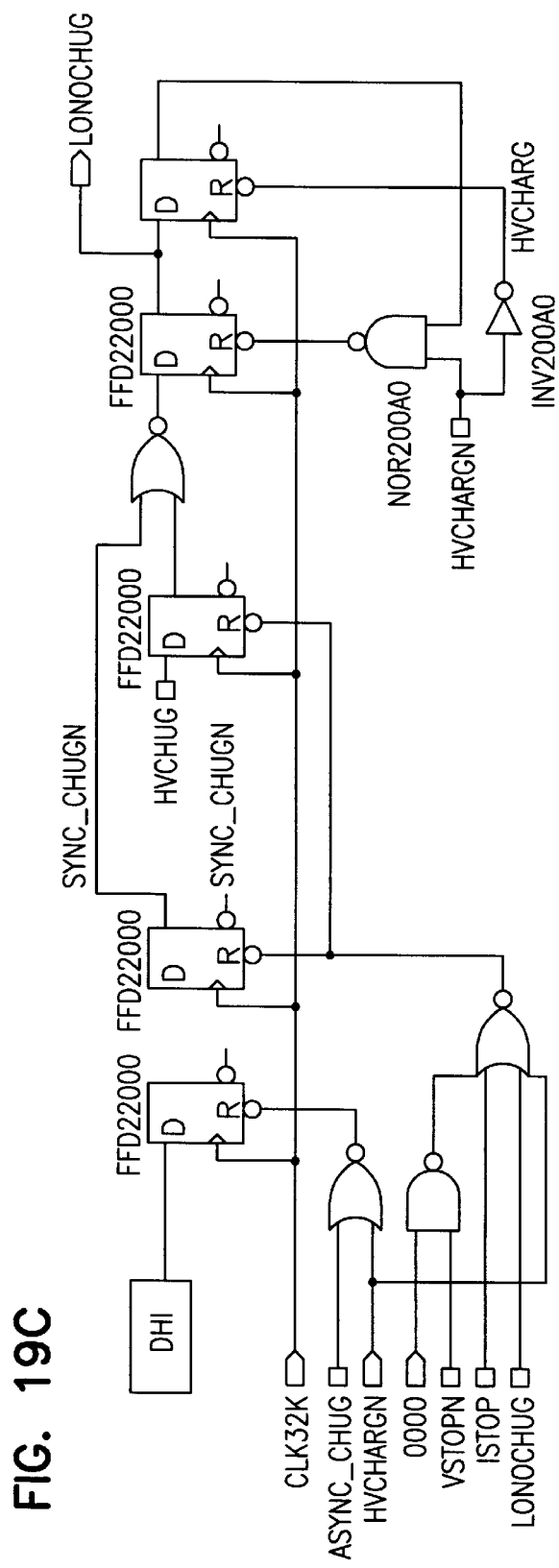

There will be some ringing when the boot signal originally goes high (immediately after the primary current is initially interrupted). This ringing may have caused some runt pulses to appear on the BOOT signal (FIG. 19), and for this reason some signal conditioning is included on the boot pad. In addition, the non-overlapping-clock device MJFNOC was included in the Boot path to further condition the signal: the MJFNOC has a re-triggerable feature that allows short positive transitions immediately after (say 100 nsec) the first negative going transition (on NOCIN) to prevent the output QN (NOCOUT) from going negative until a certain time (again about 100 nsec) has elapsed.

The falling edge of NOCOUST causes a rising edge of BOOTN which will cause BOOT_CATCH to go high (provided that it is not being held low by the reset on its flip-flop).

ISTOP

ISTOP (FIG. 12) is the usual signal that causes that causes the transformer to stop sending current through the primary, which then, in turn, causes the current to flow in the secondary.

ISTOP is generated by measuring the current flowing in the sense tap of the sensefet switch 1220. In the peak current detector circuit 1250, ISTOP is compared to a reference signal, and when the comparison conditions are met, the ISTOP signal is asserted to the HV_CHUGGER circuit.

In one embodiment, the nominal peak current that triggers ISTOP is 5 amps which provides an average current of approximately 2 amps, which is the value recommended by the battery manufacturer.

VSTOPN

VSTOPN is the signal that allows the HV_CHUGGER circuit to interrupt the primary current when the battery voltage falls below a certain predetermined point (say 2.000V). This allows reliable operation of the electronics during the last third of battery life, when the internal impedance of the battery will not sustain a 2.0 amp current draw without dropping below 2.0V; it is also the means of coping with the voltage delay phenomenon exhibited by the battery.

A way of looking at the operation of the HV_CHUGGER circuit when it is being controlled by the VSTOPN instead of ISTOP, is to consider that it regulates the input battery voltage by reducing the amount of current that is drawn from the battery. When VSTOPN terminates the primary current before the ISTOP would have interrupted it, the peak current (5 amps nominal) is not reached, and the average current will be less than 2.0 amps. Of course, when the average current is reduced, the charge time will be lengthened; as the battery becomes extremely depleted, the charge time will become so long that the effectiveness (efficacy) of the shock therapy comes into doubt, and this indicates the need to replace the device (EOL). Before EOL, but during the last half of the device life, the charging time may be used as an indicator of battery depletion. The battery voltage that is monitored for VSTOPN is called VBATFUS.

SYNC_CHUG

The SYNC_CHUG signal is generated within the HV_CHUGGER block, and performs a time-out function that will initiate a chug if too long a time has elapsed since the last chug, provided that all other conditions permit a chug to be started. These other conditions are: HVCHARGN is asserted low (HV_CHUGGER is enabled), ASYNCH_CHUG must be low (the normal command to do a chug must not be asserted), VSTOPN must be high (the battery voltage is about 2.00V). It is to be expected that ISTOP will be low (peak current can only happen if the HVCHUG signal is asserted).

Two 32 KHz clock rising edges after all the above conditions are met, the SYNCH_CHUG signal will be issued.

The primary reason that the SYNC_CHUG circuitry is required is that during the early phase of the high voltage charging sequence, the ringback voltage on the primary side of the transformer may not be sufficiently large to trip the electronics in the BOOT pad of the therapy chip. The ringback voltage in the primary is caused by the voltage stored on the parasitic capacitances. (mostly the depletion capacitance of the secondary rectifiers); this voltage on the capacitance is converted to current in the transformer and reflected back to the primary. If the voltage in the secondary is not large (say less than 20V) not enough voltage will be stored to allow the primary to go the 1.0V below the battery voltage required to trip the electronics in the BOOT detect circuit of the therapy chip.

High Voltage Output Diodes

Two high power diodes are used in the secondary to act as switches allowing energy to flow to the capacitors during the transfer stage of the charge cycle, and holding the charge on the capacitors during the primary charge stage of the charge cycle.

Battery Filter Inductor

The battery filter inductor (L1) is actually a set of three ferrite beads that give an effective inductance of 0.53 $\mu$H per bead, or 1.5 $\mu$H for a total of three beads. This inductor is optional, but when included this inductance minimizes transients generated by the switching supply and coupled to the rest of the electronics.

Charge Time

Charge time is the time it takes the high voltage power supply to charge the voltage on the output capacitors form 0 V to the final programmed value. Many cycles (hundred of thousands) of high voltage supply are required to accomplish this task and each cycle is composed of a primary charge time and a transfer time. This primary charge time should not be confused with the total charge time. Total charge time will vary with the condition of the battery. As the battery depletes, the charge time will increase and can be used as an indication of battery condition. The energy delivered out of the battery, in joules, is given by: amps out of battery times voltage of the battery while delivering the amps times the duration of delivering the amps. The charging circuit has two modes of operation:

The first mode, constant battery current mode, is evident in the fist several years of operation, and is characterized by the ability of the battery to maintain an output voltage greater than 2.0 V under a load of 2.2 amps average. This region of operation is roughly the first amp-hour of operation.

The second mode, constant battery voltage mode, is evident toward the End-Of-Life of the battery, and is characterize by the inability of the battery to maintain an output voltage greater than 2.0 V under a load of 2.2 amps. The charging circuit enters a mode of operation that regulates the amount of current drawn from the battery in such a manner that the battery voltage never falls below 2.0V. This region of operation is roughly after the first amp-hour of operation.

Peak Current Control

Figure 14:
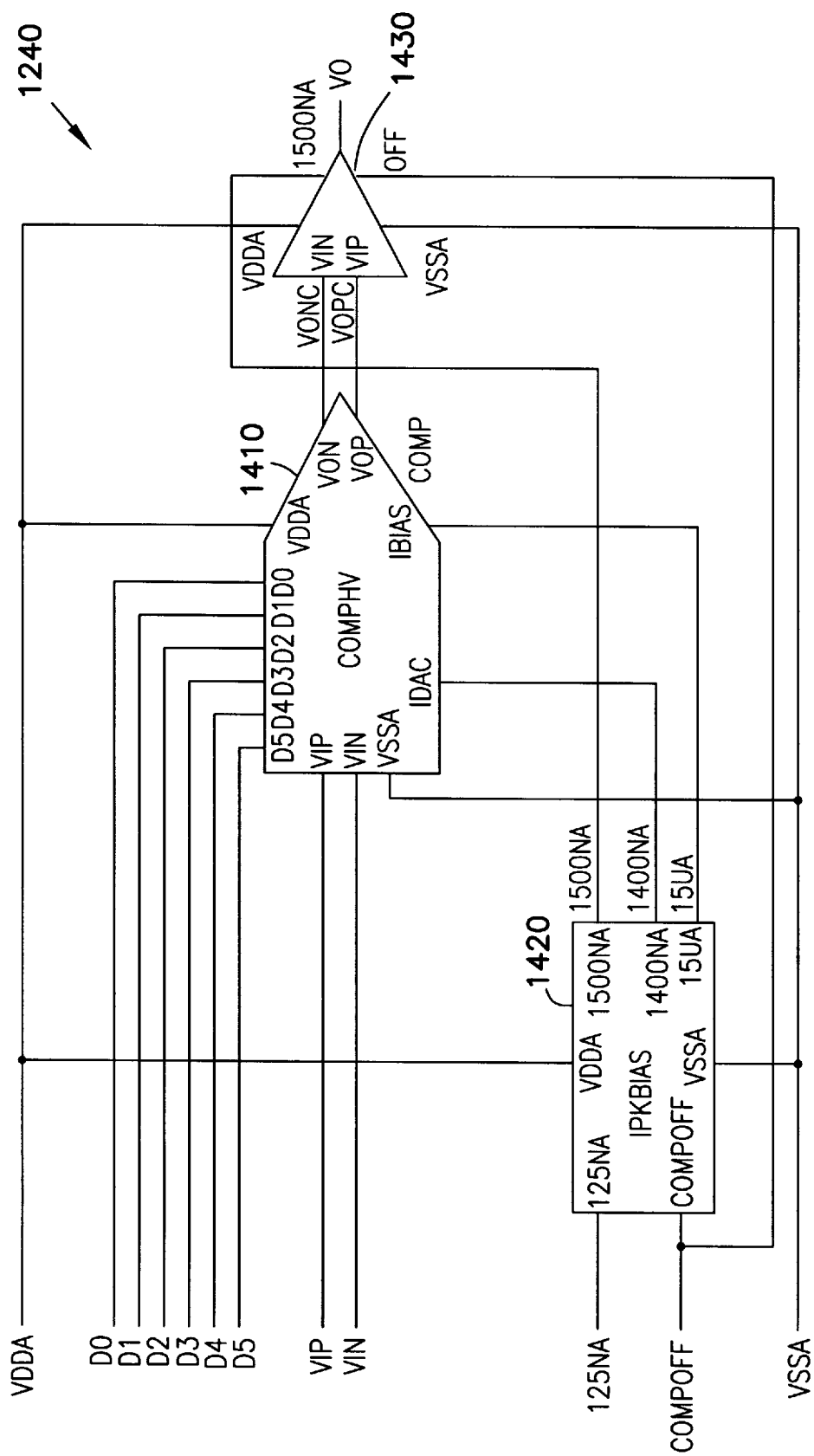
FIG. 14 is a logical block diagram a HVCOMP circuit for the voltage pulse generating system according to the present invention.

The peak value of the primary current is controlled by the circuit HVCOMP (FIG. 14). A fraction of the transformer primary current is provided by the sensefet and converted to a voltage across a trimmable 10$\Omega$ sense resistor located on the DLCC. This voltage is amplified (VOP) and compared against a reference value (VON) by HVCOMP. The output of this comparison is a digital signal (ISTOP) which is used by the digital control circuit to switch the sensefet "off".

Figure 16:
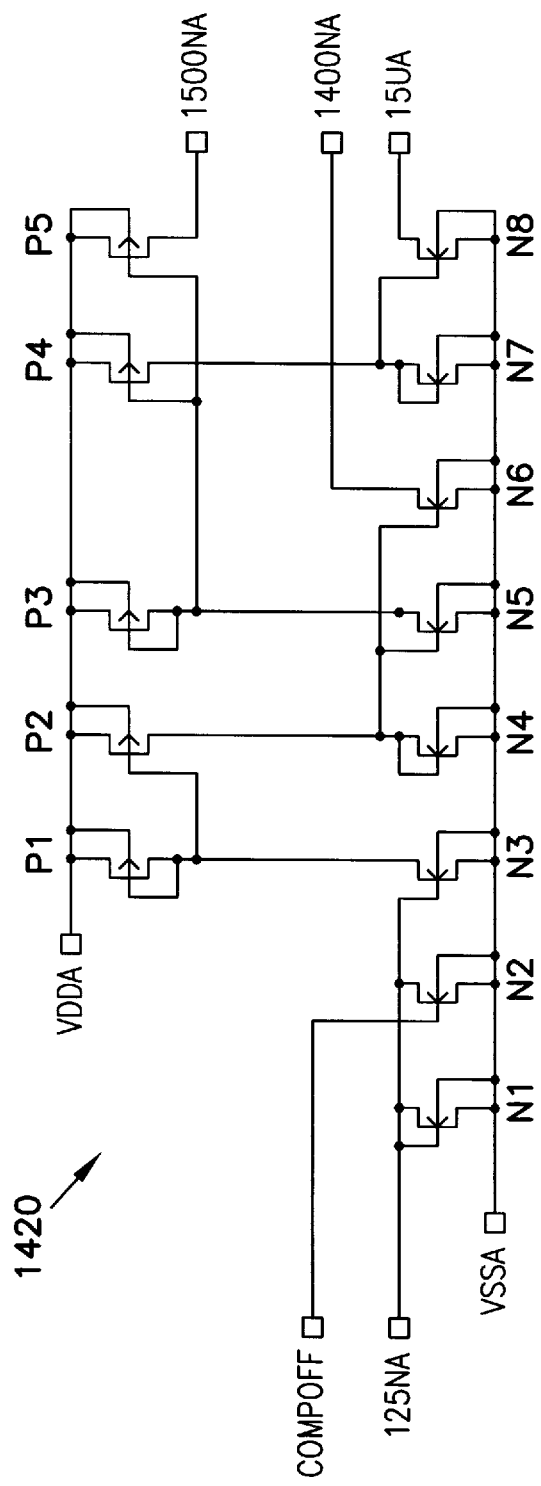
FIG. 16 is a schematic diagram of a IPKBIAS circuit for the voltage pulse generating system according to the present invention.

HVCOMP is composed of three sub-circuits; COMPHV 1410 of FIG. 14 which generates the programmable reference level and amplifies the sensed voltage, a comparator 1430, which compares the amplified voltage to the reference level and IPKBIAS 1420 (FIG. 16) which generates the currents used to bias COMPHV 1410 and comparator 1430.

Figure 15:
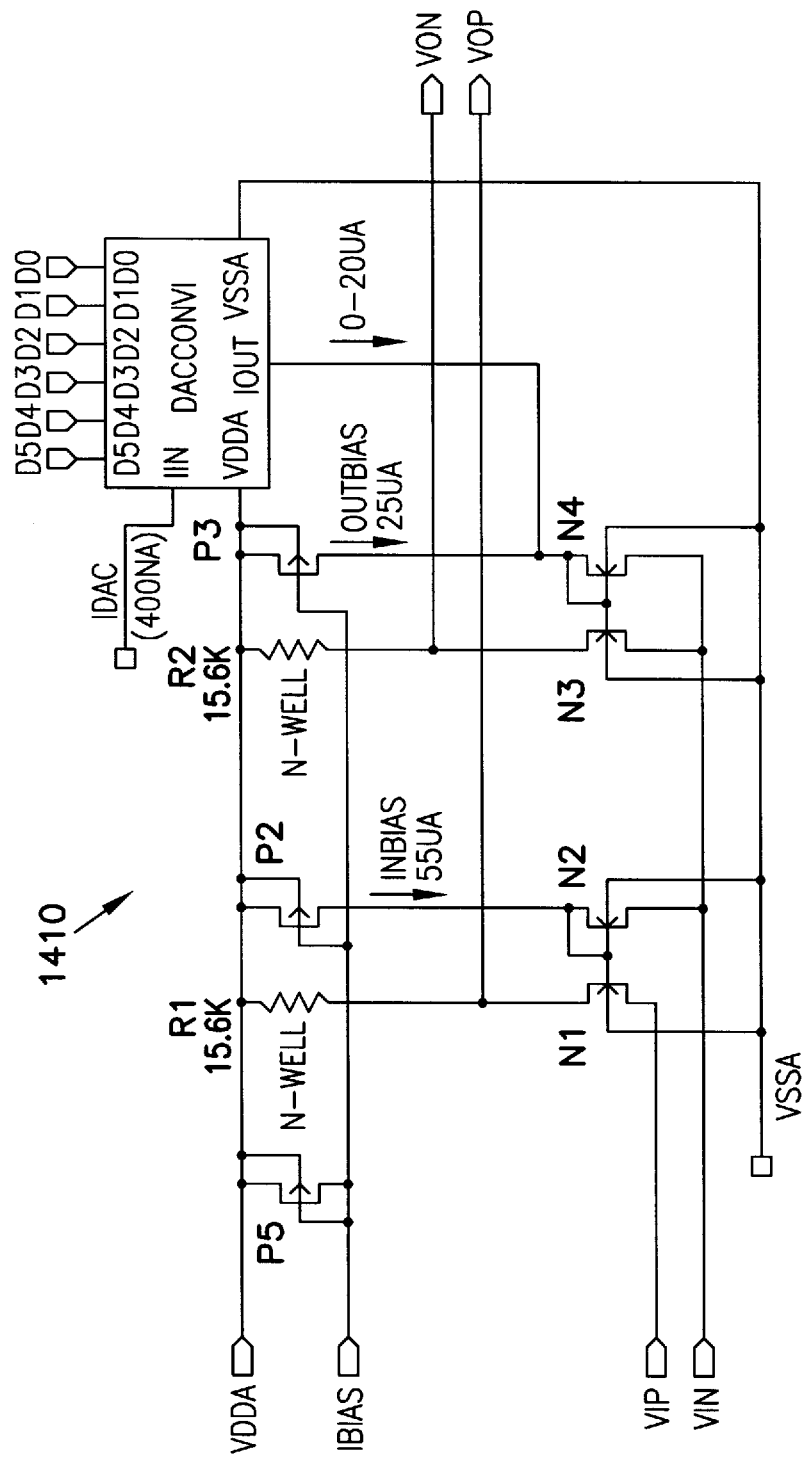
FIG. 15 is a logical block and schematic diagram of a COMPHV circuit for the voltage pulse generating system according to the present invention.

COMPHV 1410 (FIG. 15) can be broken into three sections;
1. programmable reference generator
2. digital to analog converter with current source output used to set the reference level
3. input amplifier.

The reference level is generated as a voltage drop across R2, down from VDD. Programmability is used to alter the peak current value to compensate for variances in the transformer primary inductance, the senseFet sense ration or to vary the total charge time. Since the digital control affects only the reference voltage and not the gain of the detection circuit, the gain-bandwidth of the amplifier will be constant across the range of detect levels. The speed of the comparator (trigger time) is nominally 20 nsec which results in a peak current overshoot of less than 0.25% due to this parameter.

Vtr is the voltage between IMON (VIP) and KMON (VIN) which is the voltage across the 20$\Omega$ sense resistor.

IPKBIAS 1420 (FIG. 16) takes a 25 nA current from the main current source block and multiplies it for use in biasing the COMPHV 1410 and comparator 1430 circuit. 400 nA and 5 $\mu$A current sinks in comparator 1430. IPKBIAS 1420 is controllable ON/OFF by the signal COMPOFF in order to minimize the amount of current used when the high voltage supply is not needed.

Boot Detector

Figure 17:
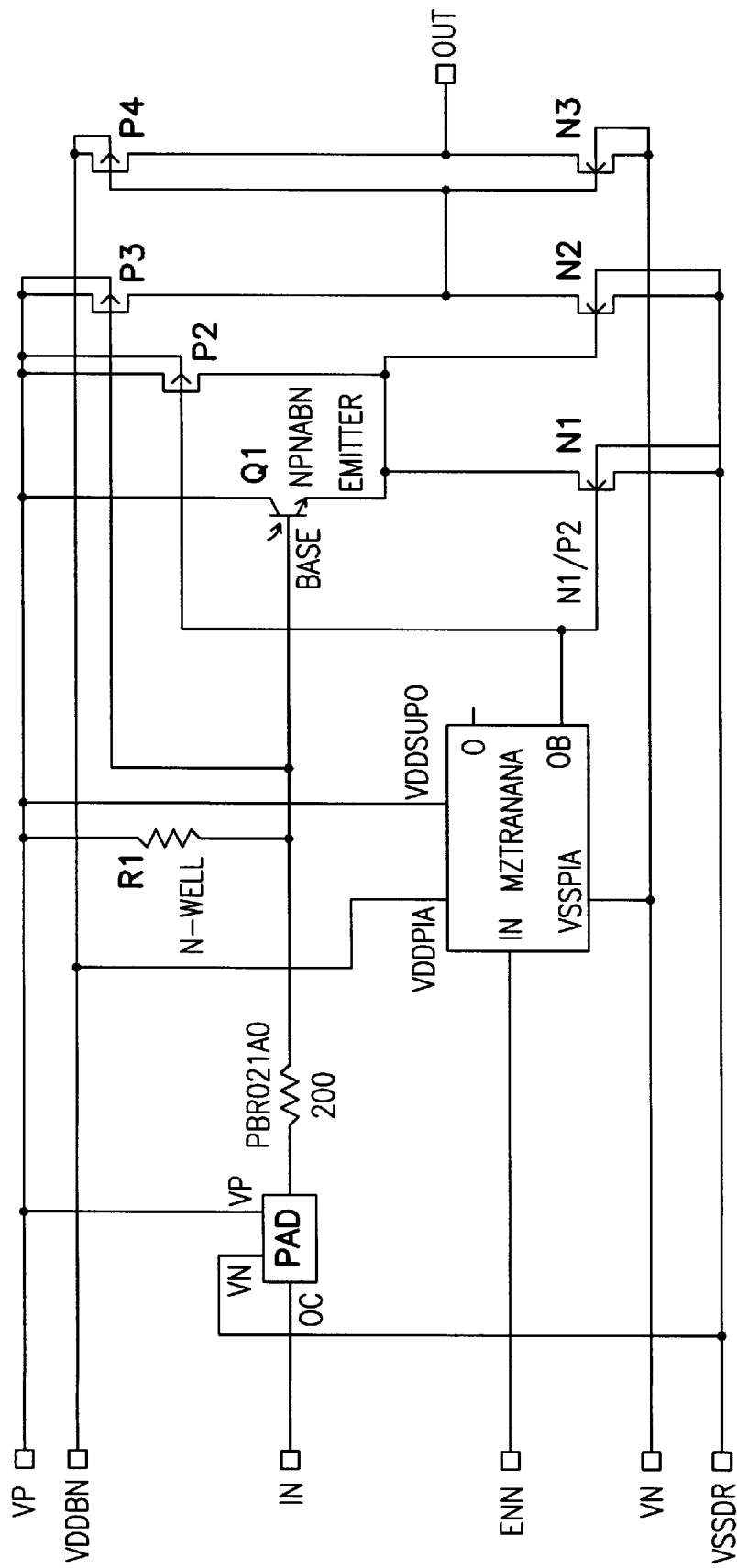
FIG. 17 is a logical block and schematic diagram of a BOOTPAD for the voltage pulse generating system according to the present invention.

The boot detector (FIG. 17) is used to detect a negative-going voltage ring on the drain of the sensefet, which occurs when the secondary diodes open, and pulls the signal BOOT low. The boot detector is connected to the drain of the sensefet through a diode (FIG. 12) which resides in the HVCC, and consists mainly of a split-input inverter and circuits which provide ON/OFF control. The voltage translator, N1 and P2 are used to turn the circuit ON/OFF and define the state of the output when the circuit is "off". R1 defines the state of the input when the circuit is "on" and the input is not pulled down by the external diode. P3 and N2 are the inverter used to detect the voltage ring and switch 1220 is used to split the input voltage into 2 levels such that P3 and N2 can both be driven off. Without switch 1220, when the input is pulled to VDD, N2 would be on and P3 would be off, which is correct. However, when the drain is at ground, the input to BOOTPAD is a diode about ground. Since P3 sees a minimum of (2V-Vdiode), it would be "on". However, N2 would see Vdiode and may not shut off, causing an indeterminate output voltage. Sifting the input voltage down by a diode would cause the opposite problem. If the input voltage were routed directly to P3, it would operate correctly, and if the input voltage were shifted down by a diode and then to N2, it would operate correctly. Note that without this diode, the circuit would operate correctly but not until the drain voltage rang a full diode below ground which would result in longer synchronous operation and therefore longer charge times would result.

The BOOT detection circuit has an input threshold of Vbatt −1.3V (nominal), this corresponds to an output (HV) voltage of approximately 127V, (1.3V*Ls/LP). Therefore, the BOOT detector operates for high voltage output greater than 127V (nominal). The BOOT signal is sent to the digital control circuit which uses it to activate another HVCHUG, thus initiating another charge cycle.

Battery Comparator Circuit

The voltage comparator in this embodiment 1260 is a high speed comparator.

HV CHUGGER

The HV_CHUGGER circuit (FIG. 19) controls the HVCHUG signal to the gate drive circuit as well as synchronizing signals as BOOT, ISTOP and VSTOP. The HV_CHUGGER circuit in turn is controlled by the master signal HVCHARGN, which indicates the start of the (roughly) 10 second high voltage charge sequence. Finer control relating to the functional operation of the circuit is accomplished by the external signals VSTOPN, ISTOP, and BOOT. Internal signal ASYNCH_CHUG is included in the design as a backup measure to help the system function in some exceptional situations.

One Example of a Chug Cycle

Figure 20:
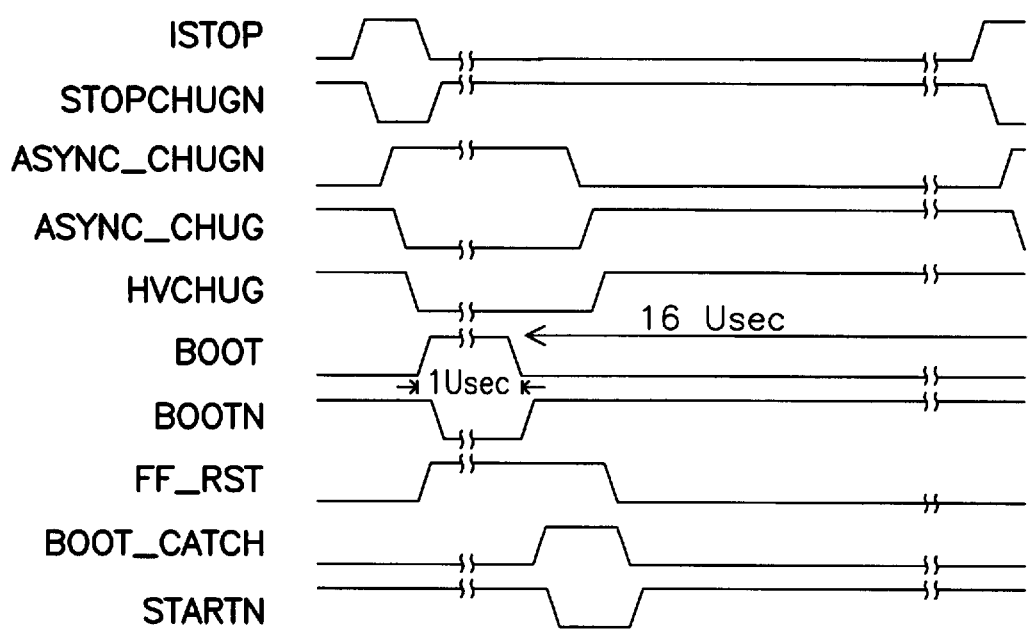
FIG. 20 is a timing diagram illustrating a typical "chug" cycle for the voltage pulse generating system according to the present invention.

To illustrate the operation of the (asynchronous) logic loop that controls the HVCHUG output signal, an example of a chug cycle will be described (FIG. 20). When the battery has adequate charge, the chug cycle is one that is controlled by the ISTOP signal; that is, plenty of battery voltage is available during the high voltage charging sequence. The sequence will be described from after the time that the HVCHUG output signal has gone high, but before the ISTOP signal is asserted. All the other cycle-stopping signals are not asserted, and will remain not asserted, during this discussion. (These other cycle-stopping signals include HVCHARGN and VSTOPN.)

Since HVCHUG is high, BOOT_CATCH will remain reset through the NOR gate, and BOOTN, will remain low because the primary is being held low by HVCHUG's action on the gate of switch 1220. When ISTOP indicates that enough current is flowing in the primary by going high, STOPCHUGN will go low which causes ASYNCH_CHUGN to go high, causing ASYNCH_CHUG to go low, which causes HVCHUG to go low (notice that STOPCHUGN going low will force SYNCH_CHUG to go low).

Soon (approximately 100 nanoseconds) after the HVCHUG goes low, the gate of the switch 1220 will go low which will cut off the current in the transformer primary and incidentally remove the condition that caused ISTOP to trigger, so that STOPCHUGN will no longer be asserted low; also, the hold that the HVCHUG had on the reset of the BOOT-CATCH latch is now released. Now the voltage on the drain of switch 1220 will go high as the transformer tries to find a path for current to flow to maintain the flux in the core; this voltage will cause the signal BOOT to go high, which causes BOOTN to go low. When the transformer has dumped all its energy into the shock capacitors (and parasitics), the ringback starts; when the ringback, as seen in the primary, crosses the threshold of the BOOT pad's signal conditioning circuitry, BOOT goes low causing BOOTN to go high, which causes BOOTN_CATCH to go high (recall that the reset on the BOOT_CATCH latch has been released). BOOT_CATCH going high will cause the latch ASYNCH_CHUGN to become set (STOPCHUGN is high since ISTOP is not asserted), which causes HVCHUG to go high. HVCHUG going high will cause a reset of BOOT_LATCH; this brings the description of the cycle back to the point where the description of the cycle was started.

Microprocessor-Based Acquisition

An alternate embodiment of the dedicated hardware design includes a processor for acquiring nibbling data and for processing nibbling data for elective replacement indication. Both total charge cycle time and nibbling time are accumulated by the processor. The processor also includes a real time clock in alternate embodiments. Another embodiment monitors battery depth of discharge by storing a predetermined battery output voltage characteristic and compares the battery output voltage and current to determine the depth of discharge. Alternate embodiments also include a monitor for detection of the energy stored in the output device, which facilitates determination of back end nibbling.

Elective Replacement Indicators and Elective Replacement Time

The following is a discussion of some of the elective replacement indicators, ERIs, which exist in several alternate embodiments of the present battery management system. Other ERIs are possible without departing from the scope and spirit of the present invention. The ERIs are discussed in the first embodiment of the power management system, however, alternate embodiments of the present power management system include these ERIs, and the demonstration of these ERIs in the first embodiment is not intended in a limiting or exclusive sense.

Back End Nibbling ERI

In one embodiment end of battery life is declared any time where back end nibbling is detected by microprocessor 600. Microprocessor 600 determines back end nibbling by testing whether the nibbling function is invoked toward the end of the charge cycle. This is accomplished by having a program running on microprocessor 600 monitor and compare the inputs from comparator 300 to determine when the nibbling function is invoked. If nibbling is detected within a predetermined percentage of the end of the charge cycle, then ERT is declared and the device is programmed to beep to warn the patient. The end of a charge cycle is determined by a signal from sense circuit 175 to microprocessor 600. In alternate embodiments the device has a status register which records the back end nibbling event for study by the patient's doctor.

Total Nibble Time ERI

In another embodiment, the microprocessor 600 records and accumulates the nibble time over a charge cycle. For example, if the accumulated nibble time over a charge cycle exceeds one second end of battery life is declared in one embodiment. The amount of total nibbling time may vary from the numbers given above without departing from the scope and spirit of the present invention, and that the numbers given are used to provide a reasonable example for demonstrating declaration of end of battery life for this embodiment of the present invention.

Nibble time is tracked by the microprocessor 600 by accumulating the length of time that the comparator indicates that the battery voltage, Vb, is less than the threshold voltage, Vth. A nibble time counter may be used to store the total nibble time per charge cycle. The nibble time counter may be reset after the charge cycle is completed, as indicated by sense circuit 175 to microprocessor 600. Alternate embodiments provide for storage of total nibble time over various therapy events and capacitor recharge events to assist in characterization of battery lifetime.

Total Charge Cycle Time ERI

Another method of indicating elective replacement is to preselect a maximum total charge time which will be tolerated by the patient and declaring ERT if the total charge time exceeds the predetermined maximum total charge time. The duration of total charge time may be monitored during therapy delivery events and capacitor recharge events.

The total charge cycle time is recorded by storing the time at which the pulse delivery is requested (whether for therapy or for capacitor recharge) and then subtracting the time upon which sense circuit 175 detects end of the charge cycle. In alternate embodiments, a counter is set up to count pulses of a known pulserate as the charge cycle begins and until the charge cycle ends. The accumulated number of pulses is then compared to the number of pulses required to reach 32 seconds based on the known pulserate. If the charge cycle time exceeds 32 seconds, ERT is declared.

The total charge cycle time ERI may employ a number of seconds which differs from 32 seconds, and the selection of the maximum charge cycle time depends on the particular application of the present invention, the patient's conditions, and a variety of other factors. The times given here and the methods of calculating them may vary without departing from the scope of the present invention.

Battery Characteristic Operating Curve ERI

Another embodiment provides an ERI which determines the battery depth of discharge (i.e., that portion of the battery characteristic operating curve in which the battery is operating). This ERI requires a knowledge of the battery characteristics.

For example, the battery characteristic open circuit output voltage curve of FIG. 2 shows a relatively moderate slope in region A, a relatively sharp slope in the early stages of region B, an extremely mild slope in the region of 0.8 to 1.2 ampere hours in region B, and a relatively sharp slope in the transition from region B to region C. The open circuit voltage and the expected slope for each of the regions of the operating curve provide references for determination of battery age under this embodiment of the present power management system.

Other batteries may have substantially different characteristic operating curves, and the teachings described herein may be applied to different operating curves without departing from the scope of the present invention.

Figure 11:
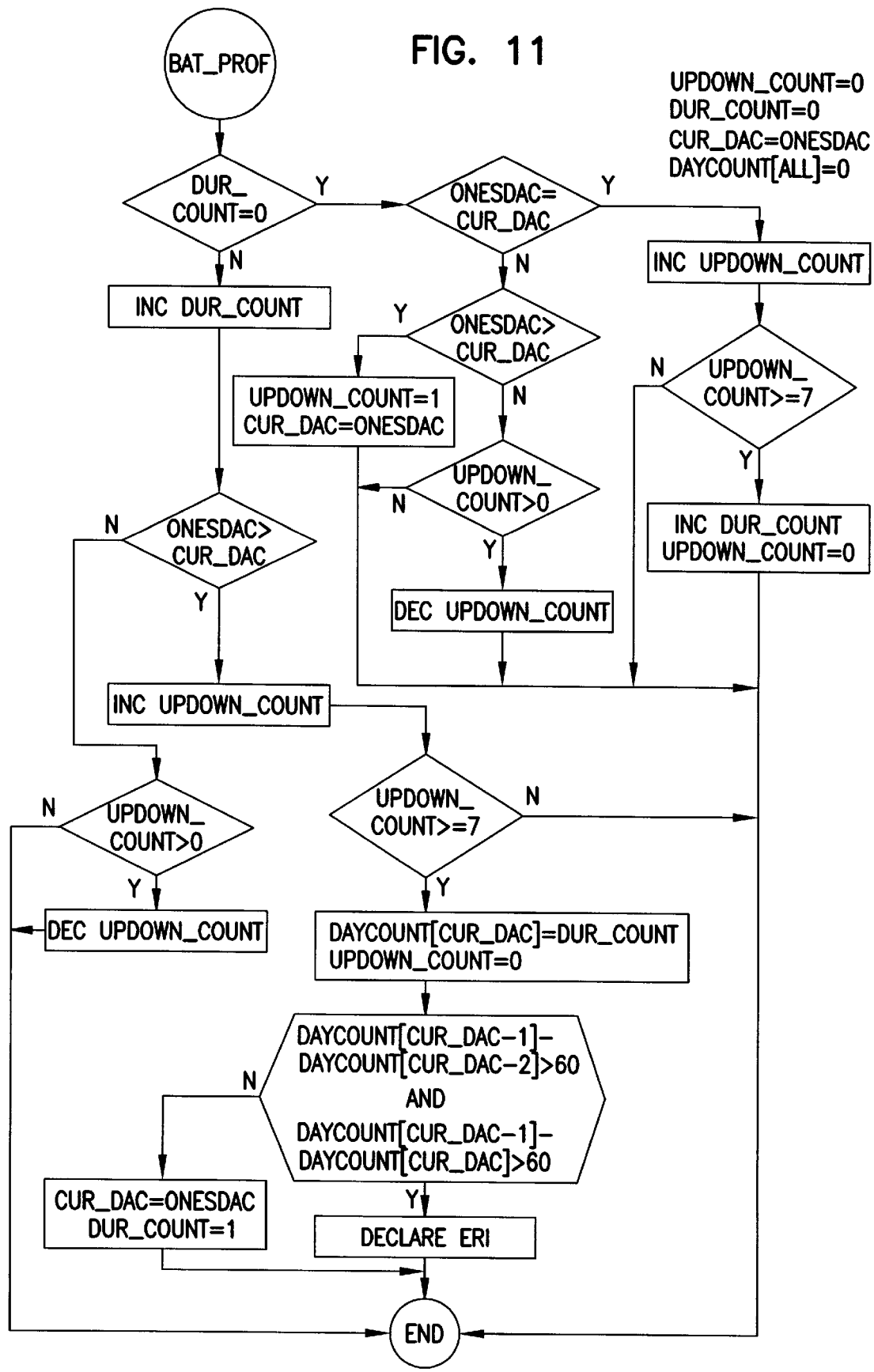
FIG. 11 is flow chart of the battery characterization system according to one embodiment of the present invention.

The system for measuring the depth of discharge of the battery and for estimating the expected lifetime of the battery is shown in FIG. 6 and the system operation is described in the flow chart of FIG. 11. This embodiment of the battery management system incorporates an updown counter ("updown_count") to compensate for environmental and circuit noise, and a traveling time voltage monitor to find the knee of the battery characteristic curve, labeled as "K" on FIG. 2. The shape of the battery characteristic curve shown in FIG. 2 is used to demonstrate this ERI.

The flat part of the battery characteristic curve just before the knee point K takes about one year of normal device usage to pass. However, once the knee point K is reached, the slope of the discharge curve becomes very steep. The device ERI is targeted to detect the knee point K on the battery characteristic curve.

As stated above, the voltage of the batteries 110 is measured with DAC 620. DAC 620 has finite quantization levels due to the limited number of bits available for conversion. In one embodiment the DAC quantization value is 100 millivolts. The open circuit voltage, Vb, is measured and compared to the battery characteristic open circuit operation curve, such as FIG. 2. Since any open circuit voltage measurement may involve some uncertainty due to environmental (such as temperature fluctuation) or circuit noise, multiple systems are incorporated to guard against single abnormal readings. As the batteries 110 age, the open circuit output voltage is continually decreasing. However, voltage variations must be monitored carefully to eliminate readings which are erroneous.

One embodiment ignores erroneous readings by waiting until seven readings are accumulated within the next DAC quantization value, however, erroneous readings are subtracted from the valid readings, until an accumulation of seven valid readings is obtained. This ensures that the battery open circuit output voltage is indeed decreasing and that errors are not interfering with the mapping of the battery discharge curve. Other embodiments may use a number other than 7 readings without departing from the present invention. The number 7 is used to demonstrate the operation of one system and is not intended in an exclusive or limiting sense.

An updown counter and a filter program are used to detect the 7 battery measurement readings within a predetermined voltage variation about knee point K to eliminate abnormal readings. For example, the filter removes readings which are more than one DAC quantization value in deviation from the present DAC value. The updown counter increments every time the output voltage measurement is one DAC quantization value below the present DAC value, and the counter decrements every time an output voltage measurement indicates greater than one DAC quantization deviation from the current DAC value.

The ERI is improved by determination of the knee point by using a traveling time voltage measurement system, instead of a rigid measurement targeted at a single absolute value for a battery open circuit voltage reading (for example 2.45 volts for a single battery, or 4.9 volts for a pair of batteries).

In one example, the traveling time voltage monitor measures the amount of time in which the output voltage of the battery is between the knee voltage and the knee voltage plus 100 millivolts. Based on the characteristic battery curve of FIG. 2, the knee point is declared when the voltage variation from the current DAC value to the next lower value happens in less than 100 days. The same updown counter system is used for both the beginning and the ending of the voltage dropping measurement.

Referring to FIG. 11, the "onesdac" value is the value of the DAC where comparator outputs are all logic one and is used to indicate the current battery voltage status. The present voltage measurement system may be used to establish the relationship between the DAC value as calibrated in the factory and the actual output voltage (absolute).

The present system maps the duration of time in which the output voltage remained in a particular DAC value and relates that to the curve of FIG. 2 to determine where on the battery curve the present system is operating. For example in the early portion of region B of FIG. 2 it takes three weeks for the DAC to change from $11 to $12, but in the flat portion of region B it may take three months for the one's DAC change from $18 to $19. Further down the voltage in the region C of FIG. 2 it may take only three weeks for the DAC change from $19 to $1A. A table can be generated for the time the output voltage of batteries remained in any particular DAC value. One such table is shown below:

| DAC  | Time (Days) |
|------|-------------|
| $10  | 14          |
| $11  | 15          |
| .    | .           |
| .    | .           |
| .    | .           |
| $18  | 21          |
| $19  | 110         |
| $20  | 18          |

When the slope changes from steep to flat and then to steep again, it is defined as the "knee" of the battery discharge curve, and the slope serves as an additional indicator of the knee point, as opposed to an ERI relying solely on an absolute open circuit voltage value. Since it is the "knee" we are targeting, there may exist interbattery variability in the voltage characteristic curves as to where the knee exists. The "knee finding" system from the slope of the discharge curve removes the interbattery variability.

Also, this slope measurement system may be used to correlate the DAC values with the absolute voltage of the battery in the device. If there is some bias introduced into this estimator procedure, the "slope knee finding system" also can remove the dependency of the DAC to any particular absolute voltage reading. Since it is the time spent on a DAC value (time for the voltage to drop 100 mv) which is important to decide the knee.

Furthermore, to deal with environmental and circuit noise such as the sensitivity of voltage reading upon temperature an updown counter can be used to ascertain a downward DAC transition. Only when the updown counter reaches a predetermined number (for example 7) a true transition will be ascertained and a second duration daycounter will start. The duration daycounter will always start and stop when the updown counter reached its critical value (e.g., 7).

ERI Summary

The above-described ERIs are intended as demonstrations of some of the applications of the present power management system, and are not exclusive or limiting. Furthermore, these ERIs in their many possible variations may be used in combination to provide a redundant ERI system for battery powered devices.

Closed Loop Sampling Times

The sampling period of the comparator feedback loops in the microprocessor and hardware feedback loop embodiments must be short enough to control the switching of the current in the primary winding of the inverter/transformer. When the sampling period is large relative to the average pulse duration of pulses to the switch the battery output voltage may exhibit large overshoot about the threshold voltage due to the slow response of the feedback loop. The faster the feedback loop, the better the system will control the output voltage of the loop and the less danger of a low voltage condition.

Batteries exhibit a "voltage recovery time" or "battery healing time" which is a period of time required for the battery to recover to its open circuit voltage after a heavy current draw. In the WGL 8513 a typical battery voltage recovery time is on the order of one millisecond. The time will vary for different depths of discharge and for different batteries.

In embodiments where time is a crucial factor, such as in capacitor charging in an ICD, a feedback loop with relatively short time delay (rapid sampling) provides the least amount of nibbling time. As seen earlier, the shorter the nibbling time, the shorter a complete charge cycle. Therefore, designs which sample at periods which are longer than the battery recovery time are less efficient in that a significant amount of time is expended in waiting for the loop to detect that the battery voltage is above the threshold voltage.

The software feedback embodiment described above has a sampling period about 100 microseconds and the hardware feedback embodiment has a sampling time of approximately 10 microseconds. Therefore both of these embodiments have feedback loops with sampling periods which are substantially shorter than the one millisecond battery voltage recovery time of the WGL 8513 battery and provide excellent battery output voltage control.

Other feedback loop periods are possible, depending on the particular a battery voltage recovery time, without departing from the scope of the invention, and the examples given herein are for demonstrating some embodiments. These examples are not to be taken in a limiting or exclusive sense. For example, other batteries may exhibit shorter periods for battery voltage recovery. In such systems, the sampling time is decreased to provide better control of the output voltage of the batteries. Additionally, battery voltage recovery times may change over the life of a battery. A variable rate sampling embodiment adapts to the change in voltage recovery time over the life of the battery.

Conclusion

One skilled in the art will readily recognize that the present power management system is applicable to any battery powered device. The use of the circuit in an implantable cardioverter/defibrillator was used to demonstrate one application of several possible applications and is not intended in an exclusive or limiting sense.

Other embodiments of the present invention are possible without departing from the scope and spirit of the present invention. For example, the present invention is applicable to systems using different batteries, different battery voltages, different battery configurations, and systems having different switching waveforms and switching frequencies. The present system can be modified to track the entire history of nibbling for other diagnostic reasons. The microprocessor embodiment may be modified by downloading new program code via telemetry link, without having to explant the device. Energy levels for pulse therapy and capacitor reformation times are programmably adjustable using the microprocessor embodiment. Alternate embodiments feature automatic capacitor reformation period adjustments for the various stages of battery life to conserve power at the end of battery lifetime.

Yet another embodiment features a first threshold voltage level which is lower than a second threshold voltage level. Hysteresis is introduced into the nibbler design by deactivating the switch signal when the battery voltage drops below the first threshold voltage and enabling the switch signal only after the battery voltage has exceeded the second threshold voltage level. This provides extra voltage margin for the batteries to extend the period of oscillation of the battery voltage about the threshold voltages, and thereby provide slower switching of the comparator. Such a hysteresis is generally undesirable, but may be necessary to avoid oscillation in extremely fast response nibbling hardware circuits.

Although specific embodiments have been illustrated and described herein, it will be appreciated by those of ordinary skill in the art that any arrangement which is calculated to achieve the same purpose may be substituted for the specific embodiment shown. This application is intended to cover any adaptations or variations of the present invention. Therefore, it is manifestly intended that this invention be limited only by the claims and the equivalents thereof.

We claim:

1. A method for delivering energy to a load from a battery having an output voltage, comprising the steps of:
   comparing the output voltage to a threshold voltage using a controller;
   if the output voltage exceeds the threshold voltage, delivering energy to the load; and
   if the output voltage falls below the threshold voltage, terminating delivery of energy to the load until the output voltage exceeds the threshold voltage, wherein the threshold voltage is greater than a reset voltage of the controller and the step of comparing is repeated in less than a voltage recovery time.

2. The method of claim 1,
   wherein the step of delivering energy comprises the step of switching the load across the battery, and
   wherein the step of terminating delivery of energy comprises the step of disconnecting the load from the battery.

3. The method of claim 2,
   wherein the step of switching comprises the step of repeatedly switching the load across the battery while the output voltage exceeds the threshold voltage, and
   wherein the step of disconnecting comprises the step of disconnecting the load from the battery while the output voltage remains below the threshold voltage.

4. The method of claim 1, further comprising the steps of:
   monitoring a current drawn from the battery while delivering energy to the load; and if the current exceeds a maximum value, then decreasing the current drawn from the battery.

5. The method of claim 4, wherein the step of decreasing the current includes the step of disconnecting the load from the battery.

6. A power manager, comprising:

a power supply including one or more batteries having output terminals and an output voltage across the output terminals, the one or more batteries having a voltage recovery time;

a comparator, monitoring the output voltage of the power supply, having an output signal which is a first signal when the output voltage of the power supply is below a selected threshold voltage and a second signal when the output voltage of the power supply is above or equal to the selected threshold voltage;

a switch, connected to the power supply, for switching a load across the power supply, the switch receiving an input signal to close and open the switch; and a controller, receiving the output signal of the comparator and transmitting the input signal to the switch to open and close the switch, wherein the controller closes the switch to provide power to the load when receiving the second signal and opens the switch when receiving the first signal, wherein the power manager provides a minimum switching time which is less than the voltage recovery time.

7. The power manager of claim 6 further comprising a latch which receives the output signal of the comparator and stores the first signal, wherein the controller is a microprocessor which periodically checks the latch and the output signal from the comparator to determine if the switch should be opened.

8. The power manager of claim 6 further comprising a latch which receives the output signal of the comparator and stores the first signal, wherein the controller is a microprocessor which is interrupted when the latch stores the first signal from the comparator and wherein the microprocessor reads both the latch and the output signal from the comparator to determine if the switch should be opened.

9. The power manager of claim 8, wherein switching is performed in less than 500 microseconds by the microprocessor.

10. The power manager of claim 6, wherein the load is an inverter having a capacitive storage device which is repeatedly switched to charge the capacitive storage device and wherein the controller is a hardware comparator loop.

11. The power manager of claim 10, wherein the switching time is a fixed period.

12. The power manager of claim 10, wherein the switching time is a function of a fixed period and current through the inverter.

13. The power manager of claim 10, wherein the switching time is a function of a fixed period, current through the inverter, and output voltage.

14. The power manager of claim 10, wherein the switching is self-oscillating.

15. The power manager of claim 14, wherein the switching is performed by sensing a ringback signal from a primary coil of the inverter to initiate a subsequent switching event.

16. The power manager of claim 10 wherein the hardware comparator loop is capable of switching in less than 50 microseconds.

17. A power manager, comprising:

a power supply having output terminals and an output voltage across the output terminals;

a comparator, monitoring the output voltage of the power supply, having an output signal which is a first signal when the output voltage of the power supply is below a selected threshold voltage and a second signal when the output voltage of the power supply is above or equal to the selected threshold voltage;

a switch, connected to the power supply, for switching a load across the power supply, the switch receiving an input signal to close and open the switch;

a controller, receiving the output signal of the comparator and transmitting the input signal to the switch to open and close the switch, wherein the controller closes the switch to provide power to the load when receiving the second signal and opens the switch when receiving the first signal;

where the load is an inverter having a capacitive storage device which is repeatedly switched to charge the capacitive storage device and wherein the controller is a hardware comparator loop; and wherein the switching is self-oscillating and is performed by sensing a ringback signal from a primary coil of the inverter to initiate a subsequent switching event.

* * * * *

UNITED STATES PATENT AND TRADEMARK OFFICE
CERTIFICATE OF CORRECTION

PATENT NO.   : 5,869,970
DATED        : February 9, 1999
INVENTOR(S)  : Palm et al.

It is certified that error appears in the above-identified patent and that said Letters Patent is hereby corrected as shown below:

Column 15,
Line 57, delete "embodiment an" and insert -- embodiment of an -- therefor.

Column 23,
Line 64, delete "sensFet" and insert -- sensefet -- therefor.

Column 26,
Line 5, delete "Whether" and insert -- whether -- therefor.

Column 29,
Line 49, delete "a battery" and insert -- battery -- therefor.

Signed and Sealed this

Twenty-fourth Day of September, 2002

*Attest:*

*Attesting Officer*

JAMES E. ROGAN
*Director of the United States Patent and Trademark Office*